United States Patent
Bica-Winterling et al.

(10) Patent No.: US 8,021,374 B2
(45) Date of Patent: Sep. 20, 2011

(54) METHOD AND DEVICE FOR THE CONTROLLED DELIVERY AND PLACEMENT OF SECURING ELEMENTS IN A BODY

(75) Inventors: Eva Bica-Winterling, Newington, CT (US); Dominique D. Gonzalez, Verona, NJ (US); George J. Collard, Mahwah, NJ (US); Zhenqi Zhu, Holmdel, NJ (US); Joseph M. Grogan, Port Washington, NY (US); Rebecca S. Gonter, West Seneca, NY (US)

(73) Assignee: The Trustees of Stevens Institute of Technology, Hoboken, NJ (US)

( * ) Notice: Subject to any disclaimer, the term of this patent is extended or adjusted under 35 U.S.C. 154(b) by 542 days.

(21) Appl. No.: 11/814,765

(22) PCT Filed: Mar. 8, 2005

(86) PCT No.: PCT/US2006/008176
§ 371 (c)(1),
(2), (4) Date: Jan. 27, 2009

(87) PCT Pub. No.: WO2006/096747
PCT Pub. Date: Sep. 14, 2006

(65) Prior Publication Data
US 2010/0137884 A1    Jun. 3, 2010

Related U.S. Application Data

(60) Provisional application No. 60/659,851, filed on Mar. 8, 2005.

(51) Int. Cl.
*A61B 17/10* (2006.01)

(52) U.S. Cl. .................................................. 606/142
(58) Field of Classification Search ............... 606/75, 606/142, 143, 151, 219; 600/104; 227/175.1
See application file for complete search history.

(56) References Cited

U.S. PATENT DOCUMENTS

| | | |
|---|---|---|
| 4,101,063 A | 7/1978 | Kapitanov et al. |
| 4,516,972 A | 5/1985 | Samson |
| 4,557,265 A | 12/1985 | Andersson |
| 4,637,396 A | 1/1987 | Cook |
| 4,913,141 A | 4/1990 | Hillstead |
| 4,950,227 A | 8/1990 | Savin et al. |
| 5,147,370 A | 9/1992 | McNamara et al. |
| 5,259,395 A | 11/1993 | Li |

(Continued)

OTHER PUBLICATIONS

Written Opinion of International Searching Authority, mailed May 6, 2008, issued in related International Patent Application No. PCT/US2006/08176.

(Continued)

*Primary Examiner* — Julian Woo
(74) *Attorney, Agent, or Firm* — Greenberg Traurig

(57) ABSTRACT

A device and method for delivering a plurality of securing elements or clips to a target region in a body. Further, the method and device deliver and place a plurality of clips to secure an implant to a target region. The device allows an operator to remotely control the delivery and placement of shape memory clips to effectively and precisely fasten the clips directly to the target region, or alternatively, to use the clips to secure the implant to the target region. Advantageously, the device allows for the application of the plurality of clips from within a lumen of a vessel.

33 Claims, 30 Drawing Sheets

U.S. PATENT DOCUMENTS

| | | | |
|---|---|---|---|
| 5,281,237 A | 1/1994 | Gimpelson | |
| 5,389,103 A | 2/1995 | Melzer et al. | |
| 5,421,712 A | 6/1995 | Laing et al. | |
| 5,499,990 A | 3/1996 | Schulken et al. | |
| 5,582,616 A * | 12/1996 | Bolduc et al. | 606/143 |
| 5,681,344 A | 10/1997 | Kelly | |
| 5,716,393 A | 2/1998 | Lindenberg et al. | |
| 5,797,536 A | 8/1998 | Smith et al. | |
| 5,820,628 A | 10/1998 | Middleman et al. | |
| 5,830,221 A | 11/1998 | Stein et al. | |
| 5,916,178 A | 6/1999 | Noone et al. | |
| 5,947,983 A | 9/1999 | Solar et al. | |
| 6,001,109 A | 12/1999 | Kontos | |
| 6,336,933 B1 | 1/2002 | Parodi | |
| 6,422,010 B1 | 7/2002 | Julien | |
| 6,451,024 B1 | 9/2002 | Thompson et al. | |
| 6,626,937 B1 | 9/2003 | Cox | |
| 6,666,881 B1 | 12/2003 | Richter et al. | |
| 6,706,053 B1 | 3/2004 | Boylan et al. | |
| 6,733,521 B2 | 5/2004 | Chobotov et al. | |
| 6,761,733 B2 | 7/2004 | Chobotov et al. | |
| 6,773,454 B2 | 8/2004 | Wholey et al. | |
| 6,800,081 B2 | 10/2004 | Parodi | |
| 6,802,859 B1 | 10/2004 | Pazienza et al. | |
| 6,960,217 B2 | 11/2005 | Bolduc | |
| 7,111,769 B2 | 9/2006 | Wales et al. | |
| 2004/0030351 A1 | 2/2004 | Goldberg | |
| 2005/0004582 A1 | 1/2005 | Edoga et al. | |
| 2005/0004660 A1 | 1/2005 | Rosenbluth et al. | |

OTHER PUBLICATIONS

International Search Report of International Searching Authority, mailed May 6, 2008, issued in related International Patent Application No. PCT/US2006/08176.

* cited by examiner

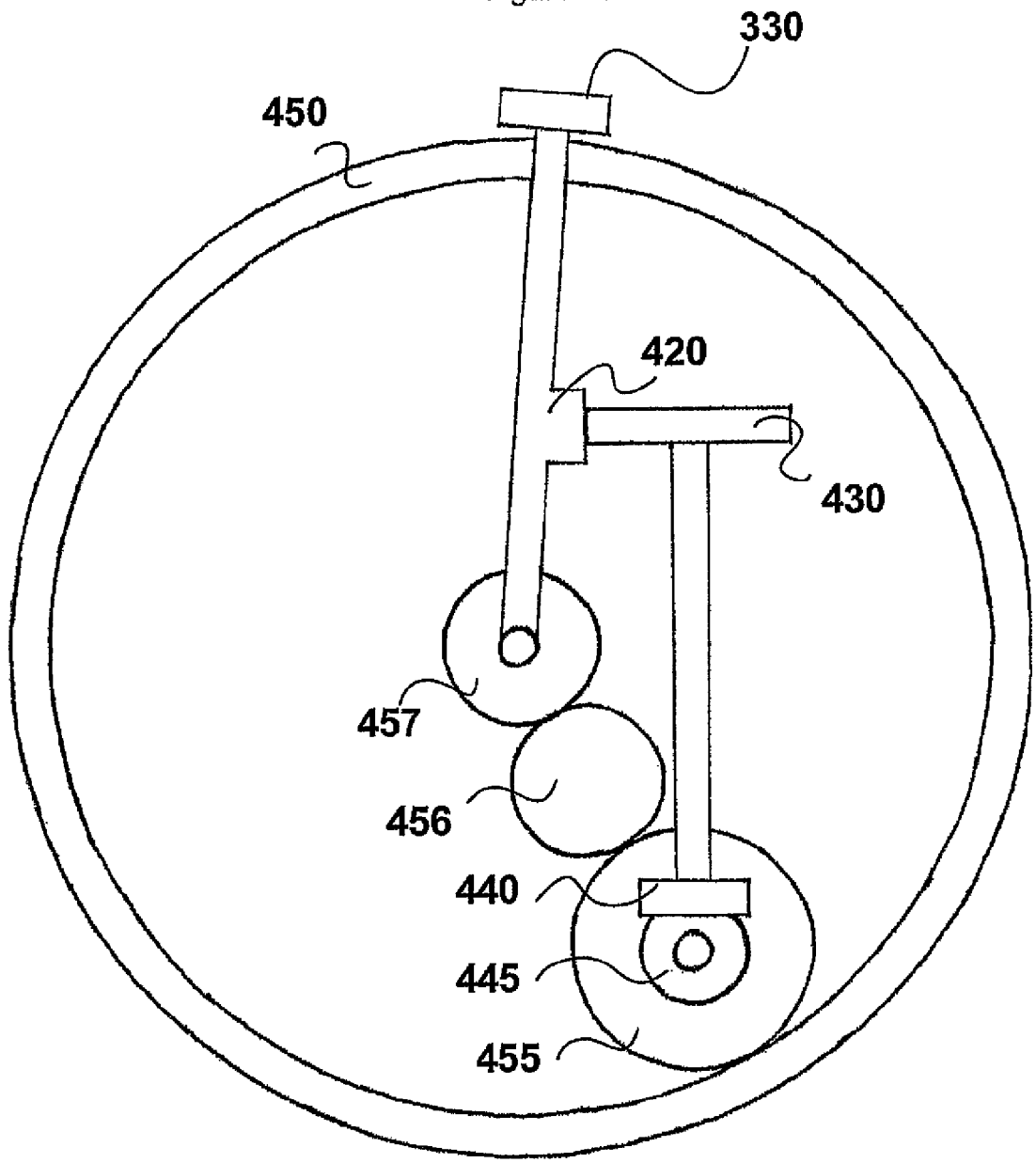

| Sequence Number | Movement of proximal end | Movement of distal end | Movement of connecting section | Mechanism movement of distal end |
|---|---|---|---|---|
| 1 | Proximal device inserted into patient | None | None | None |
| 2 | Proximal device navigated through vascular system to reach aneurysm | None | Connecting tubes follow through vascular system | None |
| 3 | Balloon inflated to secure proximal end in place | Balloon inflation Device set to approx. 6atm | Saline flows through outer saline tube to reach the balloon | Saline is pumped into distal connection of saline tube. |
| 4 | Tube 2 pushed out slightly so small bend is exposed | First Slider pushed in Order to position tube 2 | Tube 2 moves desired distance | First Slider connected to ring around tube 2 which links their motion directly |
| 5 | Tube 2 rotated until it is perpendicular with view from x-ray camera | First Dial rotated in order to position tube 2 | Tube 2 rotates by desired angle | First Dial has a keyway in its center that tube 2 lays in which causes it to rotate as First Dial is rotated |
| 6 | Tube 2 pushed out to desired position (not to exceed 90 degrees) | First Slider pushed in order to position tube 2 | Tube 2 moves desired distance | First Slider connected to ring around tube 2 which links their motion directly |
| 7 | Tube 3 moves out along with tube 2 due to lip at top of tube 3 | First Slider pushed out | Tube 3 moves out along with tube 2 | First Slider connected to ring around tube 2 which links their motion directly |
| 8 | Tube 3 pushed out until it hits stent-graft wall and needle penetrates | Second Slider pushed in order to position tube 3 | Tube 3 moves desired distance | Second Slider connected to ring around tube 3 which links their motion directly |
| 9 | Spirals are fed up and out of the needle by the rotating screw | Second Dial is rotated to deploy spiral clips | Tube 4 rotates by desired angle | Second Dial has an internal gear attached to it which rotates a series of gears that are connected to tube 4 |
| 10 | None | Second Slider is pushed to the left | None | The miter gear set is engaged |
| 11 | The needle is retracted, releasing the remainder of the spiral clip | Second Slider is pulled back | Tube 3 is retracted | Miter gears rotate which link backwards motion of Second Slider to rotation of tube 4 in the back end of the distal device |
| 12 | Tube 3 pulls back tube 2 with it as it is retracted | Second Slider pulled back | Tube 2 moves along with tube 3 | Second Slider connected to ring around tube 3 which links their motion directly |
| 13 | Clip is released | Second Slider is pulled back | Tube 2 and 3 is retracted | Miter gears rotate which link backwards motion of Second Slider to rotation of tube 4 in the back end of the distal device |
| 14 | Proximal end rotates 60 degrees | First Dial is rotated 60 degrees from original position | Tube 2 rotates 60 degrees from original position | First Dial directly connected to tube 2 via keyway, which links their motion |
| 15 | Repeat step 5 through 13 until a total of 6 clips have been placed | | | |
| 16 | Proximal end rotates 30 degrees past first placed clip | First Dial is rotated 30 degrees from original position | Tube 2 rotates 30 degrees from original position | First Dial directly connected to tube 2 via keyway, which links their motion |
| 17 | Tube 2 pushed out to desired position (must exceed 90 degrees) | First Slider pushed in order to position tube 2 | Tube 2 moves desired distance | First Slider connected to ring around tube 2 which links their motion directly |
| 18 | Repeat step 6 through 13 until a total of 6 clips have been placed | | | |
| 19 | Deflate saline balloon | Balloon inflation device releases the pressure | Saline flows through outer saline tube to drain the balloon | Saline is pumped out of distal connection of saline tube. |
| 20 | Proximal device removed from patient | None | Connecting tubes move out of vascular system | None |

Figure 21

METHOD AND DEVICE FOR THE CONTROLLED DELIVERY AND PLACEMENT OF SECURING ELEMENTS IN A BODY

CROSS-REFERENCE TO RELATED APPLICATION

This application is a U.S. National Stage Application of PCT International Application No. PCT/U.S.2006/008176, titled "Method And Device For The Controlled Delivery And Placement Of Securing Elements In A Body", filed Mar. 8, 2006, which in turn claims the benefit of U.S. Provisional Application No. 60/659,851, filed Mar. 8, 2005. PCT International Application No. PCT/U.S.2006/008176 and U.S. Provisional Application No. 60/659,851 are hereby incorporated herein by reference.

FIELD OF THE INVENTION

The present invention relates to a method and a device for remote-controlled delivery and placement of a securing element in a body. Specifically, the present invention relates to a device and a method for the delivery and controlled placement of a plurality of securing elements, such as clips, in the body during a medical procedure. The device and the method of the present invention are suited for use in laparoscopic procedures, interventional procedures, vascular surgery, endovascular procedures, arthroscopic procedures, endoscopic procedures, and other "minimally invasive" procedures.

BACKGROUND OF THE INVENTION

Conventional minimally invasive medical procedures, such as laparoscopic and interventional procedures, often require the surgeon to deliver a securing element, such as a clip, into the body. Many medical procedures require these securing elements to fix an implant, such as a stent-graft or mesh material, in a specific location in the body. For example, securing a stent-graft in place using a plurality of clips helps to prevent leaks in the stent-graft, which can compromise the efficacy of the surgical repair.

Frequently, due to the imprecision of these conventional securing element delivery techniques, the elements tend to migrate, resulting in leakage in the stents. As such, it is a goal to improve the precision with which the securing elements are placed and fixed.

One conventional device and method for delivering and fixing an implant in the body is to use a cannula loaded with the implant to the desired location. The cannula or housing is then pulled back and the implant is launched or sprung into placed, in a "jack in the box" type manner. As such, the implant is launched into place, with the surgeon having minimal control as to the placement of implant. According to another approach, the implant includes one or more hooks or other securing elements attached thereto, which upon launching, embed into the target region. Once again, because the deployment of the implant is imprecise, if the implant is improperly placed, the coupling effect of the hooks makes it difficult to remove and re-position. Still other conventional suturing techniques require two hands to grip and pull sutures in place.

Delivery and placement of securing elements is a critical part of many medical procedures, including but not limited to laparoscopic produces (e.g., hernia repair, gynecologic surgery, etc.) and other interventional procedures (e.g., minimally invasive heart surgery, etc.)

One exemplary application which involves the delivery and placement of securing elements in the body is the treatment of abdominal aortic aneurysms. The aorta is a major artery in the human body that extends from the heart down through the abdomen and branches out into other arteries that supply blood and oxygen to all organs. Due to its size and function, the aorta is commonly considered one of the most important arteries in the human body.

A healthy aorta is capable of expanding and contracting with the systole and diastole heart rhythms, allowing for the flow of blood from the heart to the body. A potentially life-threatening condition affecting one's aorta is an abdominal aortic aneurysm, an abnormal expansion or ballooning of the abdominal portion of the aorta that prevents the aorta from contracting to its normal size. Aneurysms such as this may be caused by an infection, a trauma, arteriosclerosis (a hardening and narrowing of arteries), high blood pressure, genetics, or cigarette smoking. If an abdominal aortic aneurysm ruptures, the person may experience severe and often fatal blood loss.

Presently, there are two primary surgical approaches to the treatment of an abdominal aortic aneurysm: 1) open surgery and 2) endovascular surgery. An open surgery involves making an incision from the bottom of the breastbone down to the top of the pubic bone. Following the incision, muscle and/or other organs interfering with the surgeon's access to the aneurysm are shifted out of the way so that the aorta is exposed (the aorta lies at the back of the abdominal cavity, in front of the spinal column). The aorta is clamped and the aneurysm is cut open. The open section is replaced with an aortic graft, which is sewn into place using sutures so that blood may flow through the graft.

The aneurysm sac is then sewn into place around the aortic graft to prevent the fabric of the graft from rubbing against other surrounding internal organs. This procedure provides a very secure placement of the aortic graft, resulting in a reliable treatment of abdominal aortic aneurysms.

However, due to the high level of invasiveness involved, the open procedure has a number of drawbacks. Not all patients are physically capable of undergoing an open surgery. The surgery is a highly traumatic experience for the body and typically requires a long recovery period. Furthermore, individuals with an abdominal aortic aneurysm frequently suffer from other conditions, such as lung or heart problems, that render the patient incapable of handling the trauma involved in this invasive surgical option.

Another approach to treating an abdominal aortic aneurysm involves an endovascular surgery wherein the diseased section of the aorta is replaced. This procedure is commonly referred to an endovascular stent-grafting procedure. In a standard endovascular stent-grafting procedure, a surgeon makes a small incision near the groin of the patient, and maneuvers a guide wire through the vascular system to the target aneurysm, generally with the help of x-ray technology. Then, a catheter is used to deploy a stent-graft within the body at the site of the aneurysm. With the stent-graft in place, the blood flows through the stent-graft, which is bridging the aneurysm. The stent-graft holds itself in place by gripping the healthy part of the aorta above and below the diseased portion. With blood no longer flowing through the diseased part of the aorta, the aneurysm shrinks and is no longer at risk for bursting.

Although the endovascular stent-grafting procedure is a non-invasive or minimally invasive alternative to open surgery, the procedure as currently performed lacks the reliability afforded by the open surgery. Specifically, in a conventional endovascular procedure, the stent-graft is not secured or stitched in place, but rather, the stent-graft has a radial pressure that is sufficient to hold itself in place against the aortic wall. The lack of fixation of the stent-graft creates the potential for leakage of blood around the stent-graft. A leak may occur both at a seal between the stent-graft and the wall of the aorta. This type of leak, if persistent, may require further stenting or open surgery to correct. Further, a leak may cause a backflow of blood into the aortic cavity.

Furthermore, the lack of secure fixation of the stent-graft leads to slippage or migration of the stent-graft. Generally, if migration is expected, a surgeon doctor may add extensions on the distal end of the stent-graft that extend into the bifurcation of the aorta in order to hold the stent-graft in place from the bottom. However, the added security provided by these extensions are generally ineffective and do not completely prevent migration.

These problems and others persist in the variety of medical procedures identified above. Accordingly, there is a need for a device and a method for delivering and placing a plurality of securing elements in the body for the effective implementation of laparoscopic and interventional procedures.

SUMMARY OF THE INVENTION

The present invention relates to a device and a method for the controlled delivery and placement of one or more securing elements in the body. The securing elements (e.g., clips) may be placed in a desired configuration to securely and fixedly hold an implant (e.g., a stent-graft) in place at a target region in the body during, for example, a minimally invasive procedure such as laparoscopic and interventional procedures.

The present invention relates to a remotely operated clip-delivery device that delivers a number of clips to securely fix an implant, such as an endovascular stent-grant, to a target region in the body, such as an aorta wall. Advantageously, the device and the method according to the present invention efficiently and reliably secure the implant to the target region to effectively execute any suitable medical procedure, such as, for example, the treatment of an abdominal aortic aneurysm. In addition, the clip-delivery device of the present invention allows for the application of the securing elements from within a lumen of a vessel, as opposed to application from outside the vessel.

According to an embodiment of the invention, following the placement of an implant at a target region in a patient, the clip-delivery device is inserted into the patient and navigated up to the location of the implant and target region. Once the device is in place, it positions itself against the wall of the structure and secures itself in place, using an inflatable device/mechanism, such as a balloon.

The portion of the device inserted into the body includes a plurality of pre-loaded securing elements, herein referred to as "clips." The device delivers and places the plurality of clips such that the clips penetrate the target region. In addition, the device may deliver and place the plurality of clips to secure an implant to the target region. Following delivery of each clip, the device is maneuvered to deliver the next clip loaded on the device, until all the clips have been delivered.

The clip-delivery device according to an embodiment of the present invention includes three primary devices: 1) a distal device inserted into the patient, 2) a proximal device used by the surgeon to control the operation of the distal device, and 3) a connecting system that connects the proximal device and distal device together, allowing for interaction between the two devices.

According to an embodiment of the present invention, the distal device includes a series of cooperative concentric telescoping sleeves. The sleeves possess various preformed shapes (bends) and interact with one another in such a manner that they may be mechanically extended from one another and pulled back into relation with one another.

The telescoping sleeves are arranged so as to allow precise maneuverability of the portion of the distal device upon reaching the target region. Further, the telescopic sleeves provide the distal device with a wide range of motion and control, allowing for greater accuracy in clip placement and delivery.

According to an aspect of the present invention, the clips are pre-loaded onto a screw-like extension or screw of the distal device prior to insertion into the body. The tip of the distal device may be articulated to an appropriate position for deployment of the one or more securing clips. The outside of the distal device includes an inflatable material, or balloon, inflated in order to hold the distal device in place during operation of the clip-delivery device.

According to an embodiment of the present invention, the clips are made of a suitable shape-memory wire material and are curled or spirally-shaped around an oval profile. In operation of the device, the clips may be moved through and out of the distal device by rotating the screw. According to an aspect of an embodiment of the present invention, rotation of the clips is blocked by a sleeve surrounding the screw. As such, as the screw rotates, the clips are translated upward and out of the tip of the distal device. The clip exits the device via a needle which guides the clip straight out to penetrate into the target region. The clip initially emerges from the tip of the needle in a straightened orientation, penetrates the target, and then forms a secure loop by assuming its memory shape once it is free from the constraints of the sleeve and needle of the distal device. The self-assembly or transformation of the clip into its curled memory shape causes the clip to firmly embed itself into the target region.

Next, the distal device is retracted to embed the remaining portion of the clip in the stent wall, thus securing the stent and target region together. Advantageously, the clips have one penetration point, making it easier for a surgeon to accurately deploy the clip to a desired location.

According to an embodiment of the present invention, a surgeon may use the proximal device to remotely control the distal device. According to an aspect of the invention, the proximal device includes a control assembly comprising two sliders and two dials that control the operation of the distal device via the connecting system. The motion of the slider that controls the in-and-out movement of the tip of the proximal device is linked to the rotation of the screw. As such, once a portion of the clip (e.g., half of the clip) has been placed on the outside of the aorta, a slider of the proximal device is used to retract the tip of the distal device, rotate the screw, and release the remainder of the clip into position in the implant and/or target region. Additionally, the proximal device includes a port for connection of a saline pump to administer saline to pressurize and inflate a balloon used to secure the distal device in place during operation.

The connecting system includes a series of tubes that interconnect the elements of the distal device to the control assembly (i.e., dials and sliders) of the proximal device. The connecting tubes are arranged such that movement of the controls of the proximal device results in an identical movement to the corresponding element of the distal device.

According to an embodiment of the present invention, the procedure is monitored through x-ray machines and/or cameras that detect radio-opaque markings on the device and the clips. Furthermore, the x-ray machines and/or cameras may track and monitor the position of the radio-opaque nitinol clips.

According to another embodiment of the present invention, the location and deployment of the clips may be monitored or tracked using a clip sensor located at or near the exit point of the distal device. The clip sensor detects when the clip has reached the exit point of the distal device, and communicates this information to the surgeon via an indicator located on the proximal device. Further, the clip sensor detects when the clip has been completely deployed (i.e., when the clip completely exits the device), and communicates this information to the surgeon via the indicator.

Advantageously, the clip-delivery device and the clip-delivery method according to an embodiment of the present invention combine the security of open surgery with the ease and minimal invasiveness of endovascular surgery.

BRIEF DESCRIPTION OF THE DRAWINGS

The present invention will be more readily understood from the detailed description of the preferred embodiment(s) presented below considered in conjunction with the attached drawings, of which:

FIG. 17 is an illustration of an exemplary interconnections of a proximal device, according to an embodiment of the present invention;

FIG. 21 provides an exemplary sequence of steps involved in operating a clip-delivery device, according to an embodiment of the present invention.

It is to be understood that the attached drawings are for the purpose of illustrating concepts of the present invention and may not be to scale.

DETAILED DESCRIPTION OF THE INVENTION

The present invention relates to a device and a method for delivering and placing a plurality of securing elements at or in a target region of the body. In addition, the present invention relates to a device and method for delivering and placing a plurality of securing elements to fix an implantable structure at or to a target region.

According to an embodiment of the present invention, the securing elements, herein referred to as "clips," may include any suitable biocompatible fastening mechanism, such as, for example, a clip, a staple, a suture, etc.

According to an embodiment of the present invention, an implantable structure, material, or device, herein referred to as an "implant", that may be secured at or to the target region may include any suitable implantable material, such as for example, a stent-graft, a mesh material, a sensor, etc.

Furthermore, according to an embodiment of the present invention, the "target region" may include any area of the body to which the clips are to be delivered and embedded within during the medical procedure. For example, for an abdominal aortic aneurysm procedure, the target region is the aortic wall, and the clips are used to secure an implant (e.g., a stent-graft) thereto.

According to an embodiment of the present invention, a clip-delivery device 1 (see FIG. 19) provides for the remote-controlled delivery and placement of a plurality of clips 10 (see FIGS. 1-4) directly to a target region in a body. For example, the clip-delivery device 1 may be used to tie or connect one or more segments of tissue directly together (i.e., without the use of an implant).

According to an embodiment of the present invention, the clip-delivery device 1 provides for the remote-controlled delivery and placement of a plurality of clips 10 to secure an implant at or to a target region in a body.

Figure 19:
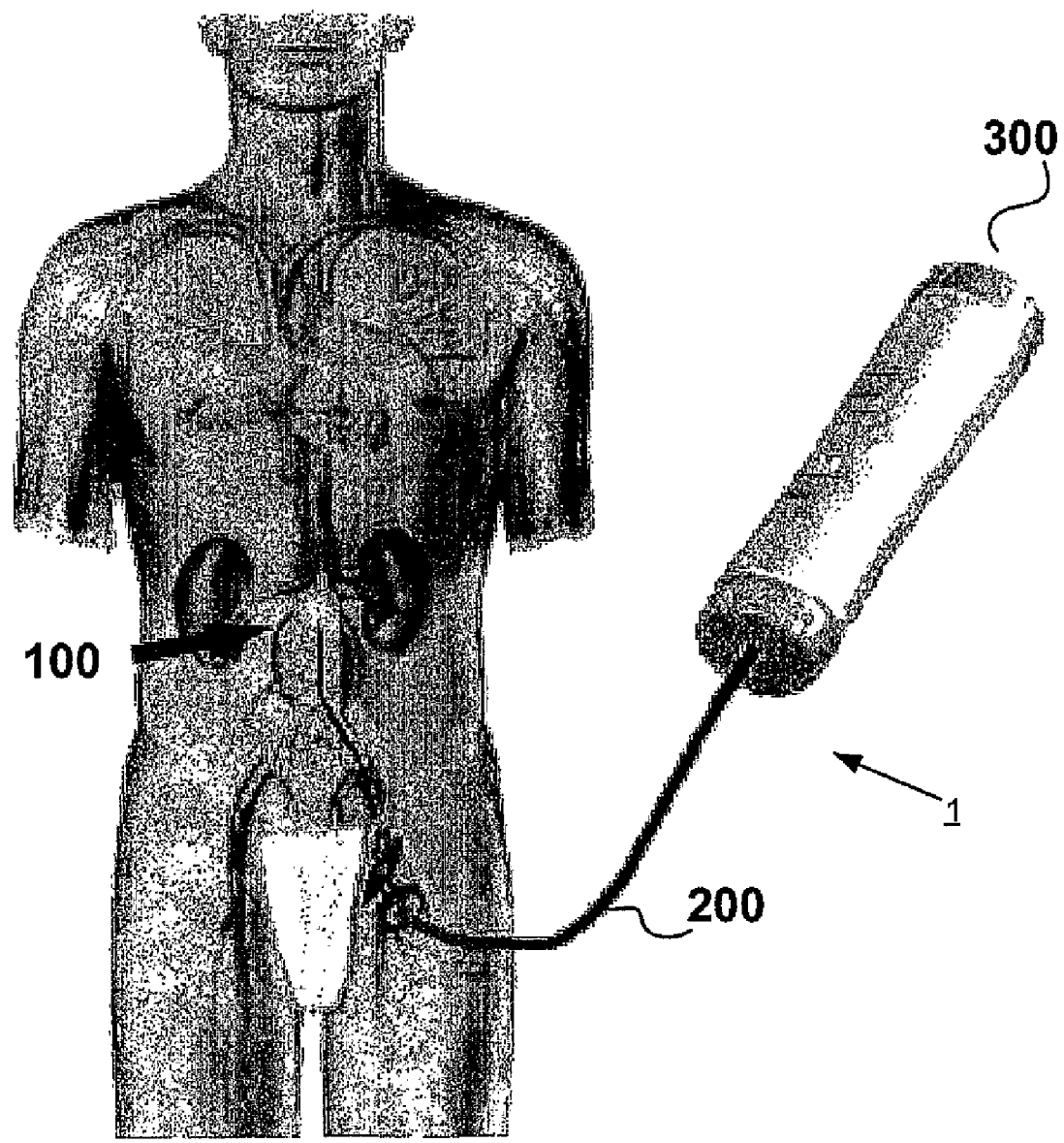
FIG. 19 is an illustration of a clip-delivery device as applied to a patient, according to an embodiment of the present invention.

According to an embodiment of the present invention, the clip-delivery device 1 includes three primary components: 1) a distal device 100 for delivering a plurality of clips 10 to securely fasten a stent-graft to the target region; 2) a proximal device 300 for remotely controlling the operation of the distal device 100; and 3) a connecting system 200 for connecting the distal device 100 and the proximal device 300, as shown in FIG. 19.

Figure 20:
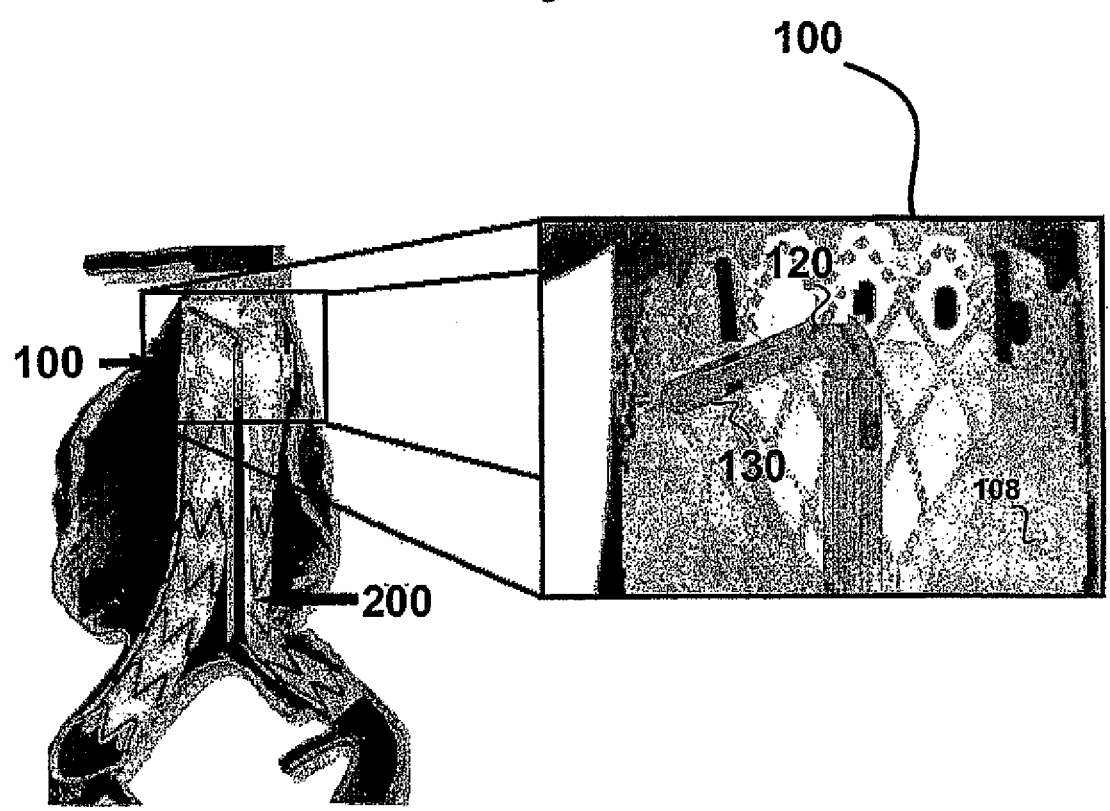
FIG. 20 is an illustration of a clip-delivery device as applied to a patient, according to an embodiment of the present invention.

According to an embodiment of the present invention, the distal device 100 is inserted into a patient, for example, via the patient's femoral artery, and navigated through the patient's vascular system to the target region and previously placed stent-graft, as shown in FIGS. 19 and 20. Once positioned, the distal device 100 securely holds itself in place at the target region, so that it may deliver the clips 10 without shifting or sliding. Preferably, the distal device 100 includes an inflatable structure, such as a balloon, that is inflated to press against the target region (e.g., the aorta wall), thereby holding the distal device 100 in place. Once secured in place, the proximal device 300 is used to control the distal device 100 in the positioning and delivery of the plurality of clips 10, as described in detail below. According to an aspect of the present invention, the distal device 100 may be any suitable shape and size and may, for example, have a total diameter of approximately 18 french (i.e., approximately 6 mm) or less.

According to an embodiment of the invention, the clips 10 are composed of any known shape-memory material. Preferably, the clips 10 are composed of nitinol wire, due to the material's superelasticity, elastic deployment, biocompatibility, kink resistance, constancy of stress, physiological compatibility, thermal deployment, dynamic interference, fatigue resistance, hysteresis, and MRI compatibility. Advantageously, nitinol may be "trained" to have a new shape, according to methods known in the art. Absent the application of an external force, the nitinol clips 10 assume this natural shape, herein referred to as its "memory" shape. Through the use of opposing forces, the nitinol clip 10 may be biased into a shape other than its memory shape. Further, removal of the opposing force allows the nitinol clip to return to its memory shape.

Figure 1:
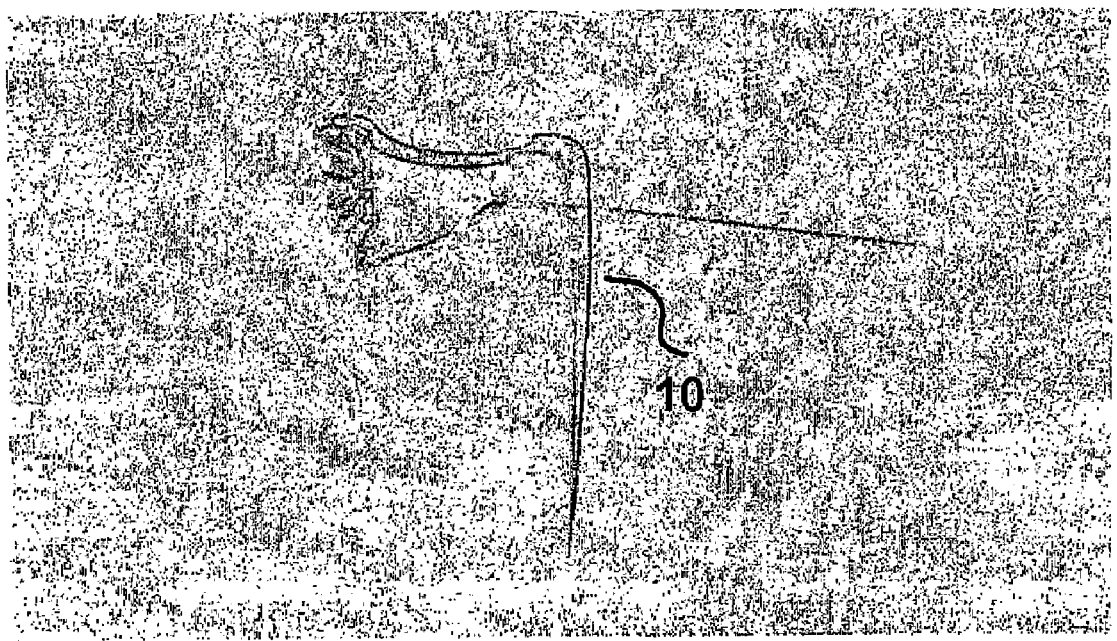
FIG. 1 is a photograph depicting an exemplary spirally-shaped nitinol clip, according to an embodiment of the present invention.
Figure 2:
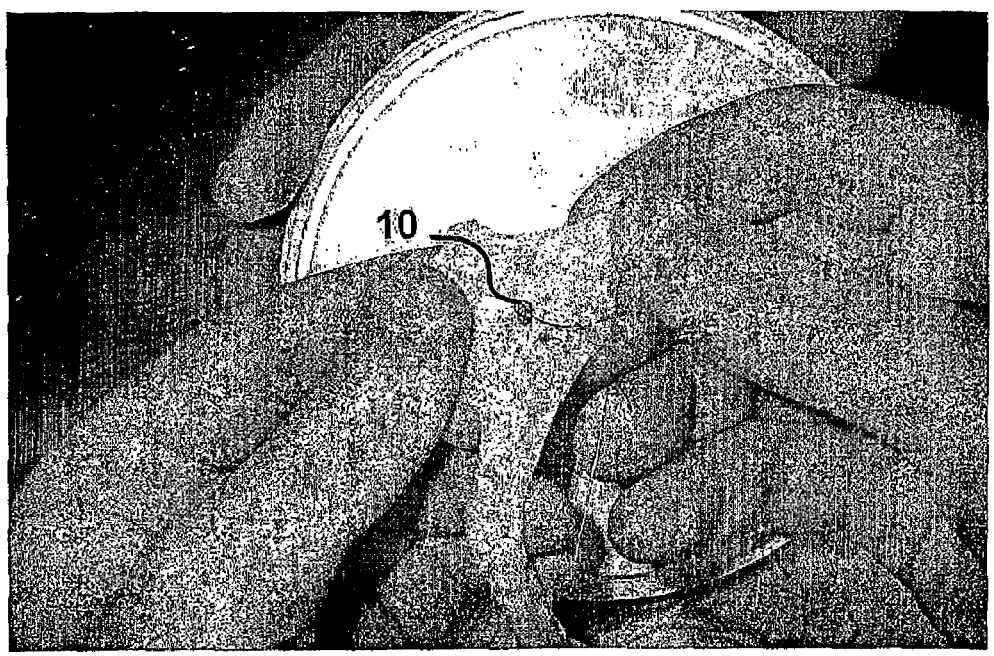
FIG. 2 depicts an exemplary spirally shaped nitinol clip penetrating an aortic wall-like material, according to an embodiment of the present invention.
Figure 3:
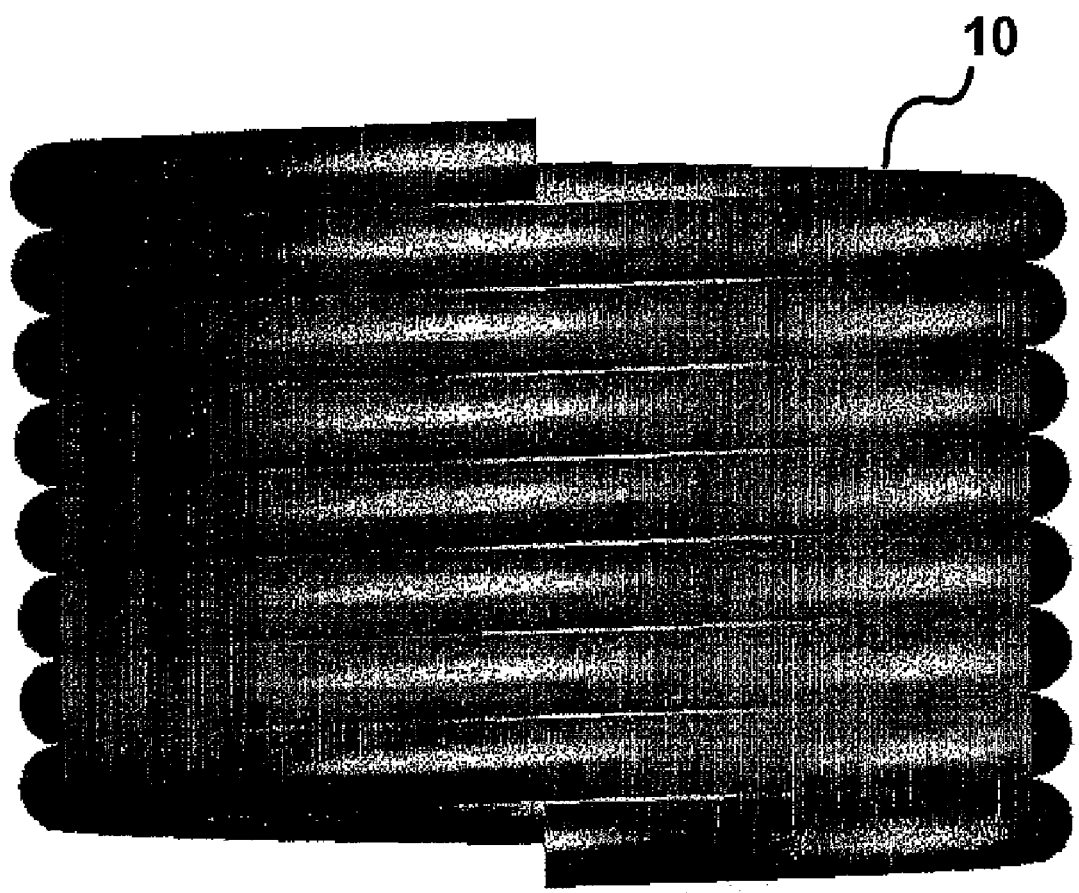
FIG. 3 is an illustration depicting a side view of an exemplary spiral clip, according to an embodiment of the present invention.

According to an embodiment of the present invention, the clips 10 are configured to have a "pigtail" or curled memory shape, as shown in FIGS. 1-3. Although described as having a curled or spiral shape, one having ordinary skill in the art will appreciate that the clips 10 may have alternative shapes. The clips 10 assume a curled configuration absent the application of an opposing force. As the clips 10 are pushed through and out of the distal device, the leading end of the clip 10 may assume a relatively straight orientation, to allow it to penetrate the implant and/or target region. According to an embodiment of the present invention, the leading end or edge of the clip 10 may be pointed or sharp to facilitate penetration into the implant and/or target region.

The substantially straight configuration is a transient state assumed by the clips 10 when exiting the device. The clips 10 are configured to re-assume the curled memory shape upon penetration into the implant and/or the target region. Advantageously, the re-configuration or movement of the clip 10 into its curled memory shape causes the clip 10 to firmly embed into the implant and/or target region. As described below, the clips 10 undergo a shape transformation due to the super-elastic properties of the shape-memory material (e.g., nitinol) to allow a user to deploy the clips 10 in a precise manner at the desired location.

Figure 4:
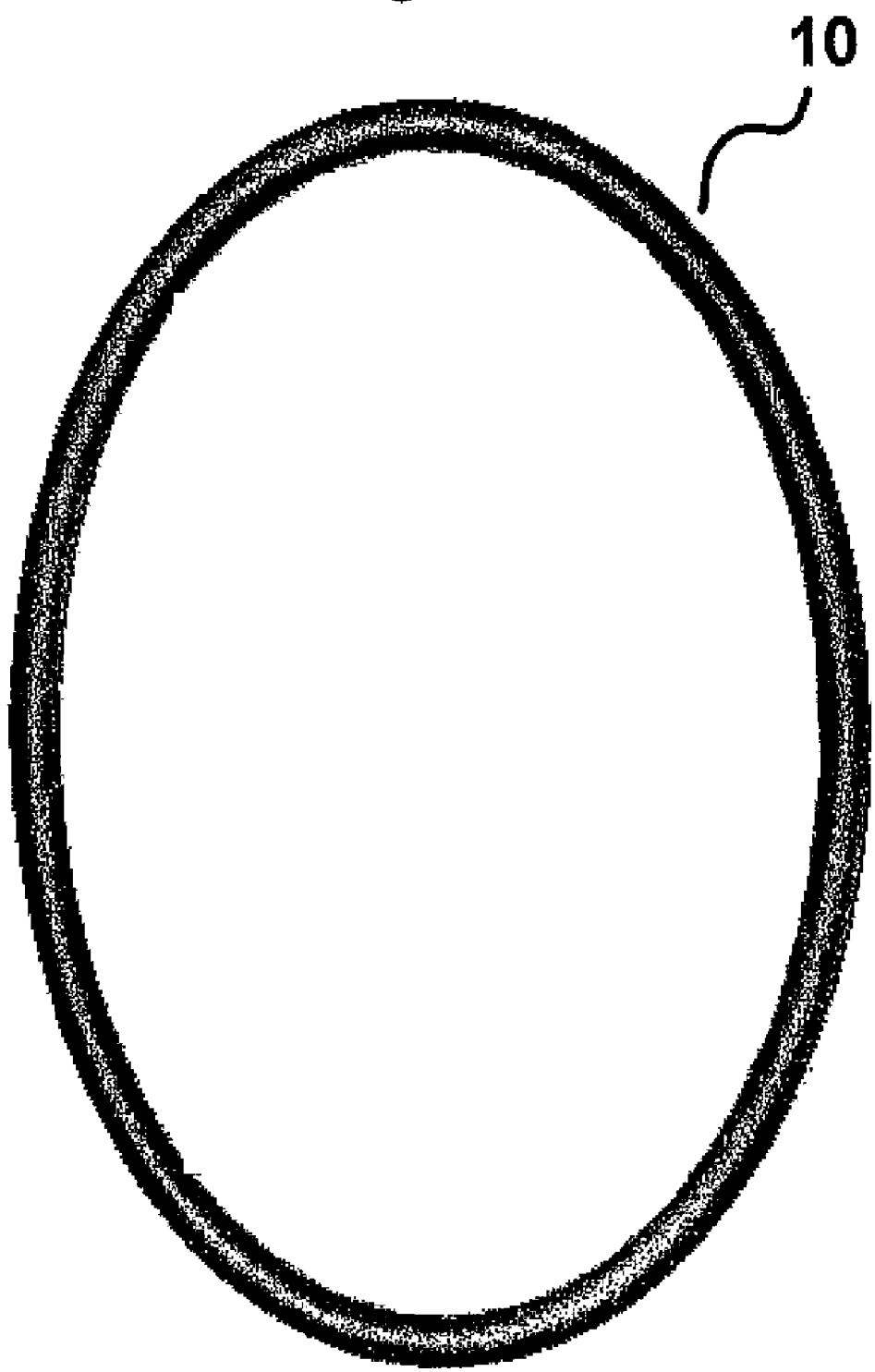
FIG. 4 is an illustration depicting a top view of an exemplary spiral clip, according to an embodiment of the present invention.

Advantageously, the clips 10 are designed to provide a suitable level of shear and normal support when secured to the target region, such that the clips 10 remain securely embedded in the target region when subjected to normal forces. Furthermore, the clips 10 may be sized such that both holding strength and ease of placement are maximized. Preferably, the spirally shaped clips 10 exhibit an oval profile, as depicted in FIGS. 3 and 4.

The spirals or curls of the clips 10 may be tightly wounded and packed, such that adjacent curls are in contact with one another. The tight packing of the spirals gives the clips 10 additional strength and robustness. Advantageously, the clips 10 have a blunt tip or leading edge, thus limiting the damage to surrounding organs, vessels, or other structures of the body in the event of accidental contact with the clip 10.

The clips 10 may be any suitable length when straightened, with the important considerations being that the clips 10 are small enough for delivery into the target region and strong enough to provide sufficient securing force upon the stent-graft. One having ordinary skill in the art will appreciate that the clips 10 may be arranged such that the spiral configuration includes any number of turns. In a preferred embodiment, each clip 10 include eight turns of wire, which when straightened, has a length of approximately 6.6 cm.

Figure 5:
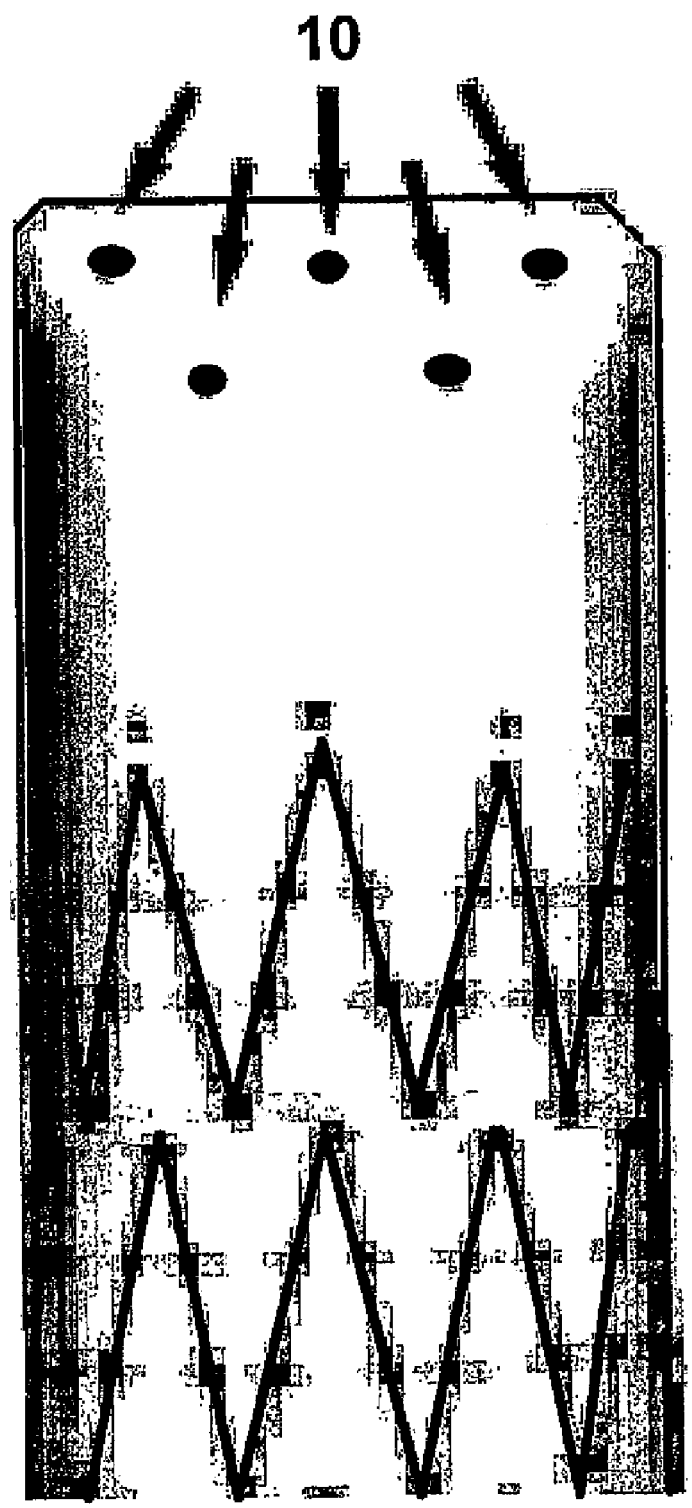
FIG. 5 is an illustration of an exemplary placement of clips on an implant, according to an embodiment of the invention.
Figure 6:
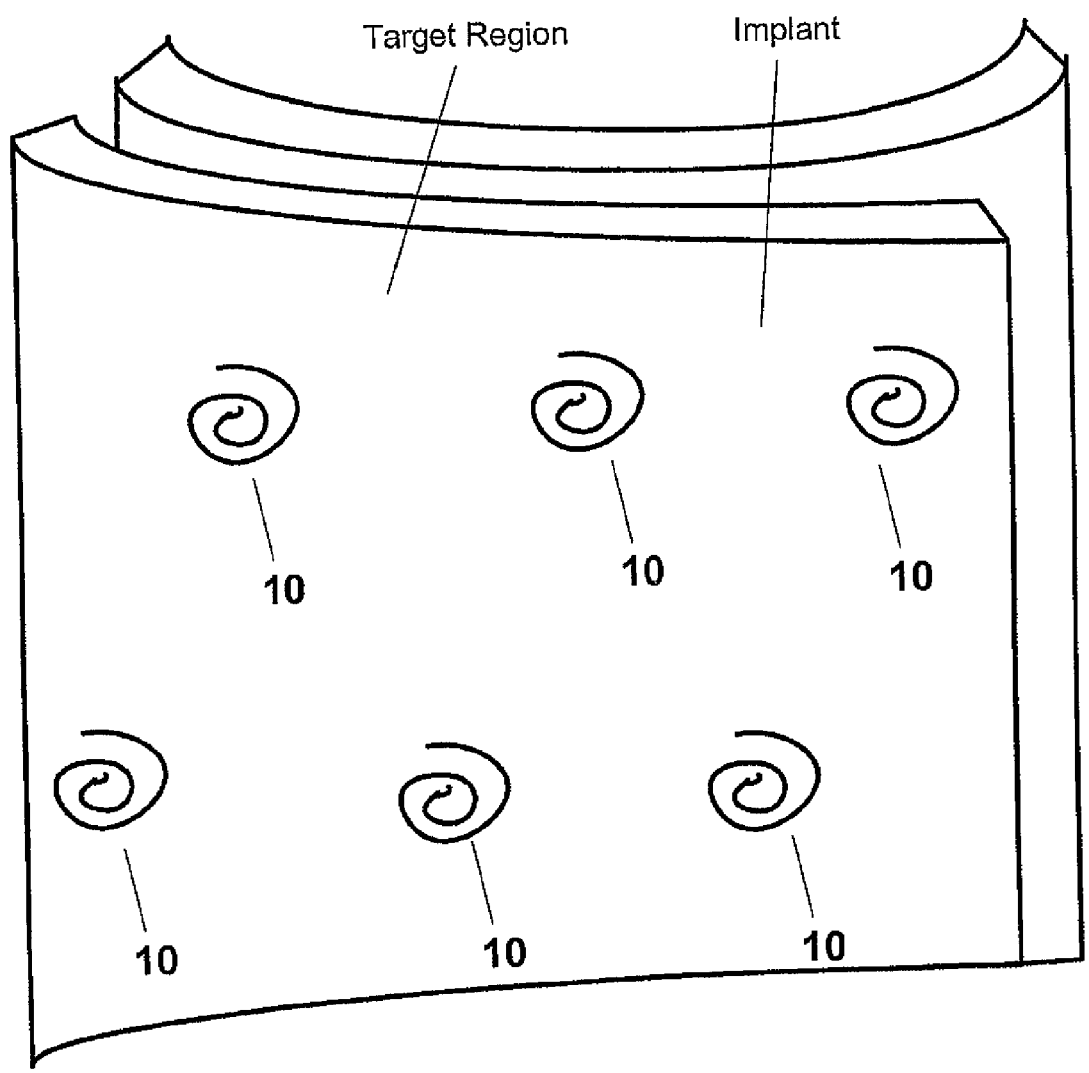
FIG. 6 is an illustration of an exemplary clip placement arrangement, according to an embodiment of the present invention.

One having ordinary skill in the art will appreciate that any number of clips 10 may be deployed to secure the implant to the target region. According to an embodiment of the present invention, a suitable number of clips 10, such as twelve, may be placed in any desired pattern (e.g., a symmetrical arrangement of clips) around the top of the implant to pin it to the target region. In a preferred embodiment, the clips 10 are arranged in two equal sets (i.e., a top and a bottom row) and are spaced and distributed to maximize the securing strength, as schematically shown in FIGS. 5 and 6. Advantageously, the clip-delivery device 1 allows for the application or deployment of the clips 10 from within a small interior space, such as the lumen of a vessel or the inner open space or cavity of a tubular organ, such as, for example, a blood vessel or an intestine. The application of clips 10 from within the lumen of a vessel allows for the use of the clip-delivery device 1 in a variety of procedures, as compared to conventional devices and approaches which are limited to application of the securing element from outside the vessel.

According to an embodiment of the invention, as the distal device 100 rotates around the target region, a clip 10 is placed approximately every 60 degrees along the top of the stent-graft, until six clips 10 have been positioned. The second row of clips 10 are placed slightly at a suitable distance below the first set. According to an embodiment of the present invention, the second set of clips 10 may be arranged in an offset position relative to the first set of clips 10, for example, at an approximately 30 degree offset from the top set of clips 10, such that each of the bottom row of clips 10 is substantially aligned with the midpoints between the clips 10 of the top row. Advantageously, this exemplary clip 10 configuration provides an even form of support for the stent-graft, as shown in FIGS. 5 and 6. One having ordinary skill in the art will appreciate that the clip-delivery device 1 allows a user to arrange the clips 10 in any suitable configuration, depending on the particular objectives of the procedure being performed.

Figure 9:
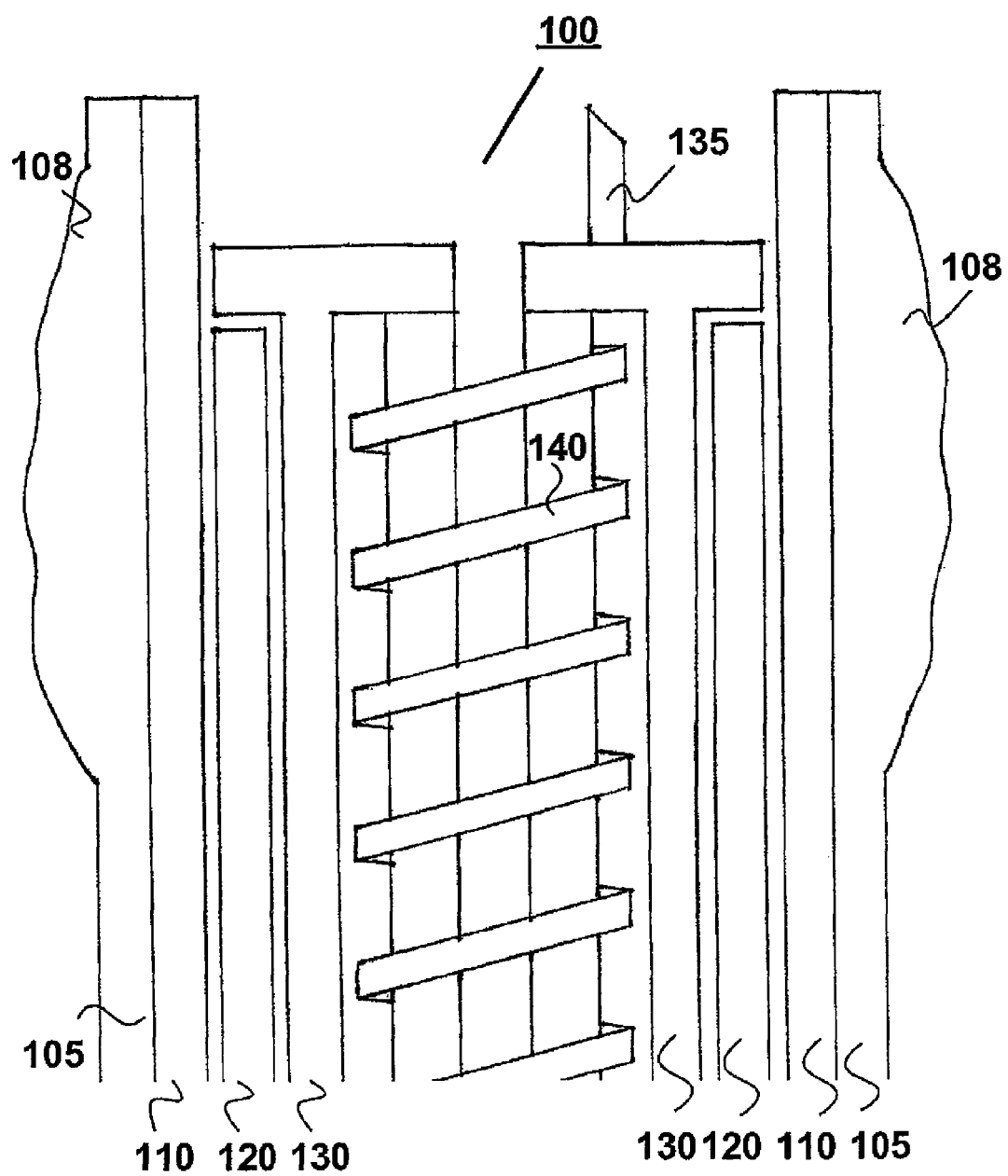
FIG. 9 is an illustration of a distal device, according to an embodiment of the present invention.

According to an embodiment of the present invention, the distal device 100 includes a plurality of telescopically arranged sleeves inserted one within the other, identified from the outermost sleeve to the innermost sleeve as: a saline sleeve 105, a first sleeve 110, a second sleeve 120, an inner screw sleeve 130, and the inner screw 140. These telescoping sleeves are inserted one within the other, in a telescoping arrangement, with the saline sleeve 105 being the outermost sleeve and the inner screw 140 being the innermost sleeve, as shown in FIG. 9.

Figure 7:
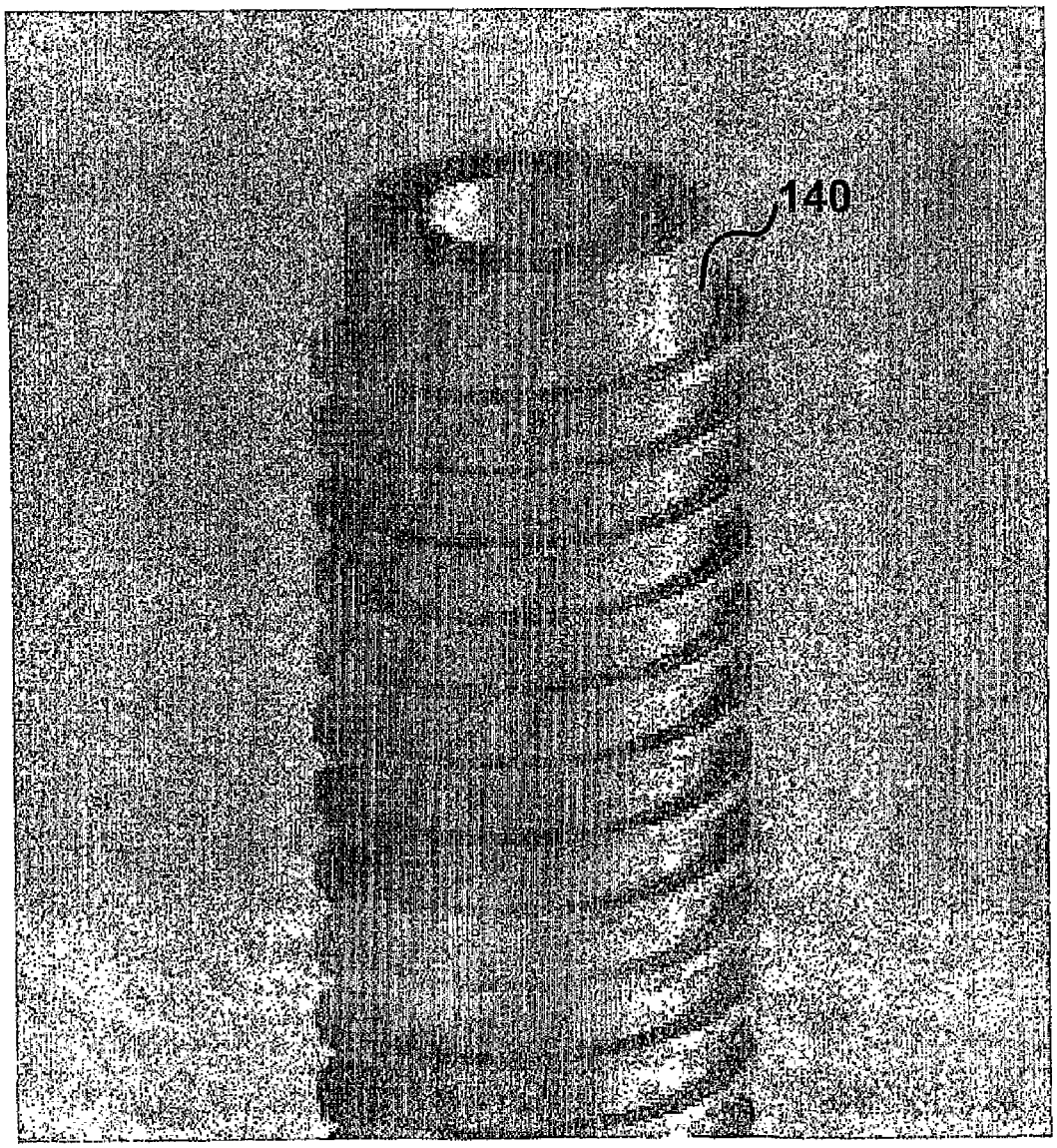
FIG. 7 is an illustration of an exemplary inner screw of a distal device, according to an embodiment of the present invention.
Figure 10:
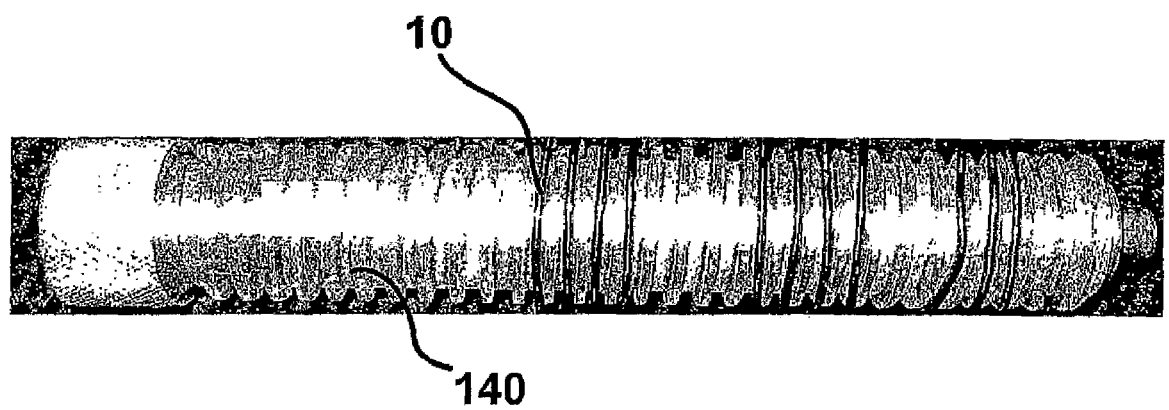
FIG. 10 is an illustration of an inner screw with a plurality of clips loaded thereon, according to an embodiment of the present invention.

The inner screw 140 is a screw-like structure onto which the clips 10 are loaded, as shown in FIG. 10. One having ordinary skill in the art will appreciate that the inner screw 140 may include a threaded outer surface including a series of threads to facilitate holding of the clips 10, as shown in FIGS. 7 and 10. An exemplary arrangement of the clips 10 loaded on the inner screw 140 is depicted in FIG. 10.

According to an embodiment of the present invention, the clips 10 are pre-loaded around the inner screw 140 prior to insertion of the distal device 100 into the body. Advantageously, the pre-loading of the clips 10 eliminates the need for the distal device 100 to be removed from the body in order to load one or more additional clips 10. Accordingly, the distal device 100 need only be removed from the patient once, upon completion of the procedure. Pre-loading the desired number of clips 10 to adequately secure the stent-graft to the target region reduces the likelihood of trauma, contamination, and infection that may result from the repeated removal and re-insertion of the distal device 100.

According to an embodiment of the present invention, the clips 10 may be arranged and loaded onto the inner screw 140 such that the clips 10 are prevented from rotating with the inner screw 140 as it turns. As such, upon rotation of the inner screw 140, the clips 10 experience a linear motion and not a rotational motion. By analogy, the relative movement of the inner screw 140 and the clips 10 is like that exhibiting by holding a nut on a bolt and rotating the bolt, thereby forcing the nut to move linearly up to the tip of the bolt.

Figure 8:
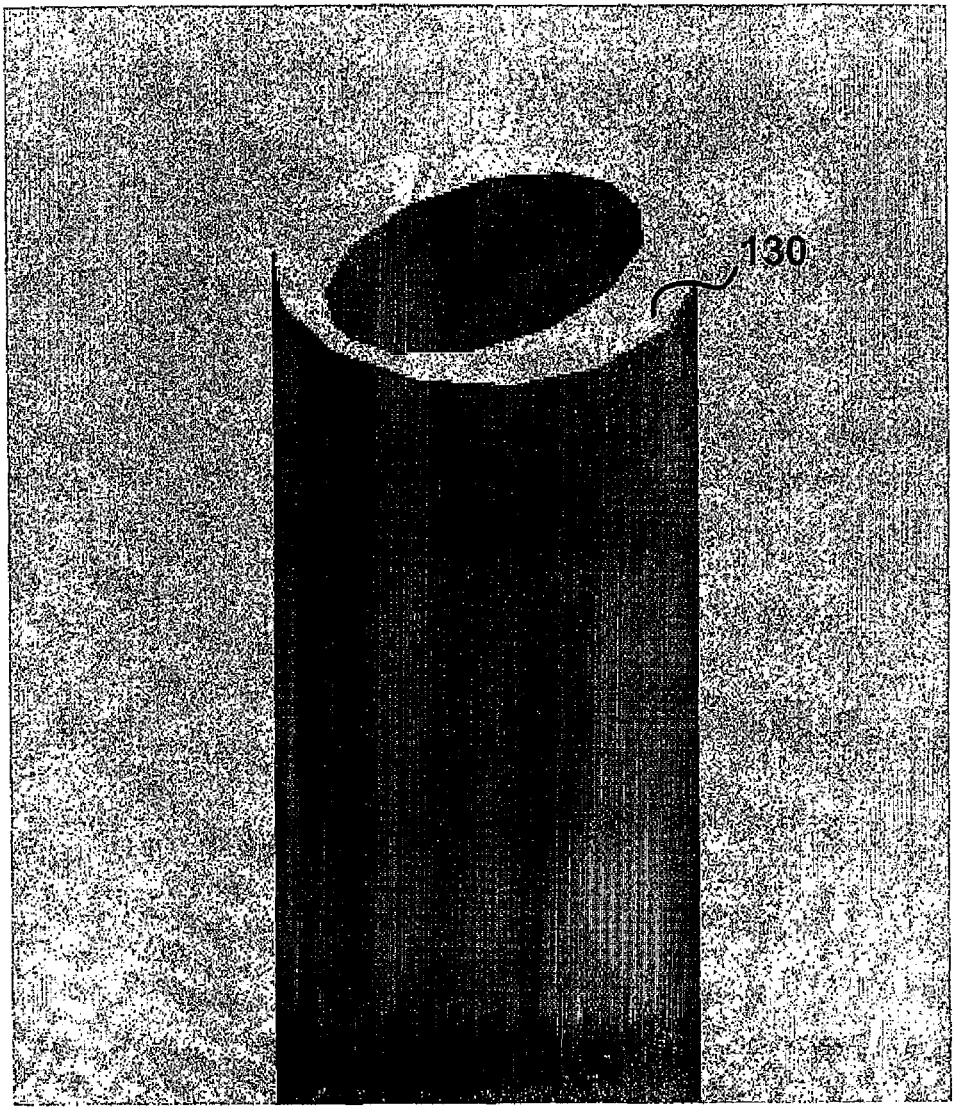
FIG. 8 is an illustration of a sleeve surrounding an inner screw, according to an embodiment of the present invention.
Figure 11:
FIG. 11 is an illustration of a sleeve that surrounds an inner screw, according to an embodiment of the invention.
Figure 12:
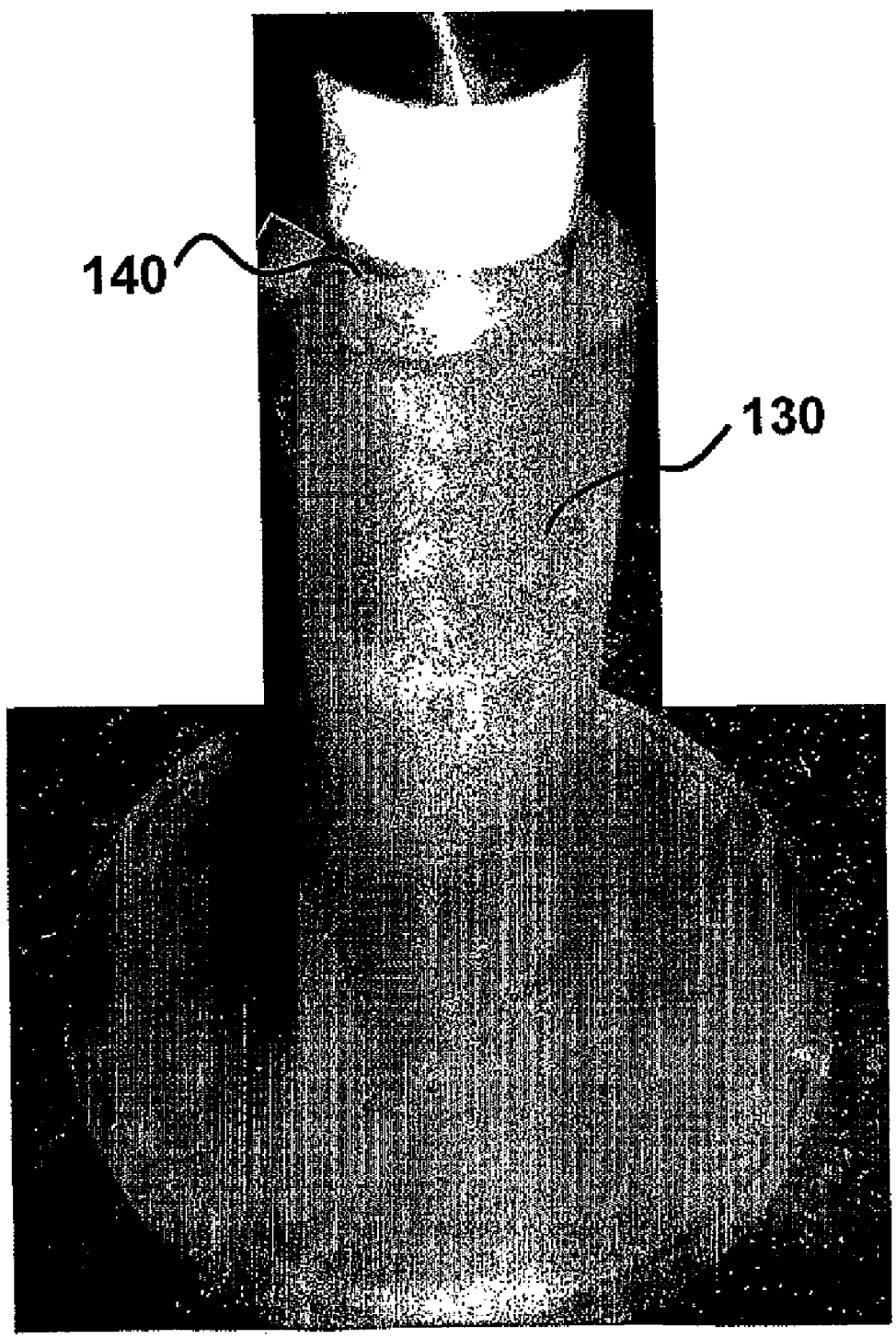
FIG. 12 is an illustration of an inner screw having a plurality of clips loaded thereon positioned with a sleeve, according to an embodiment of the present invention.

According to an embodiment of the present invention, the clips 10 are prevented from rotation with the inner screw 140 by inserting the clip-loaded inner screw 140 within the inner screw sleeve 130, as shown in FIG. 12. To prevent rotation of the clips 10, the inner screw sleeve 130 is shaped and sized to contact the clips 10 when the inner screw 130 is placed within the inner screw sleeve 130 and to provide a frictional force against rotation of the clips 10, as shown in FIG. 8. For example, for spirally-shaped clips 10 having an oval profile, the inner screw sleeve 140 may also have a non-circular or oval shape, as shown in FIG. 11. When the inner screw 140 turns, the clips 10 may attempt to rotate with the inner screw 140, but are prevented from doing so by the interior wall of the inner screw sleeve 130. An exemplary inner screw 140 and inner screw sleeve 130 according to an embodiment of the invention are depicted in FIGS. 7 and 8, respectively.

Figure 13:
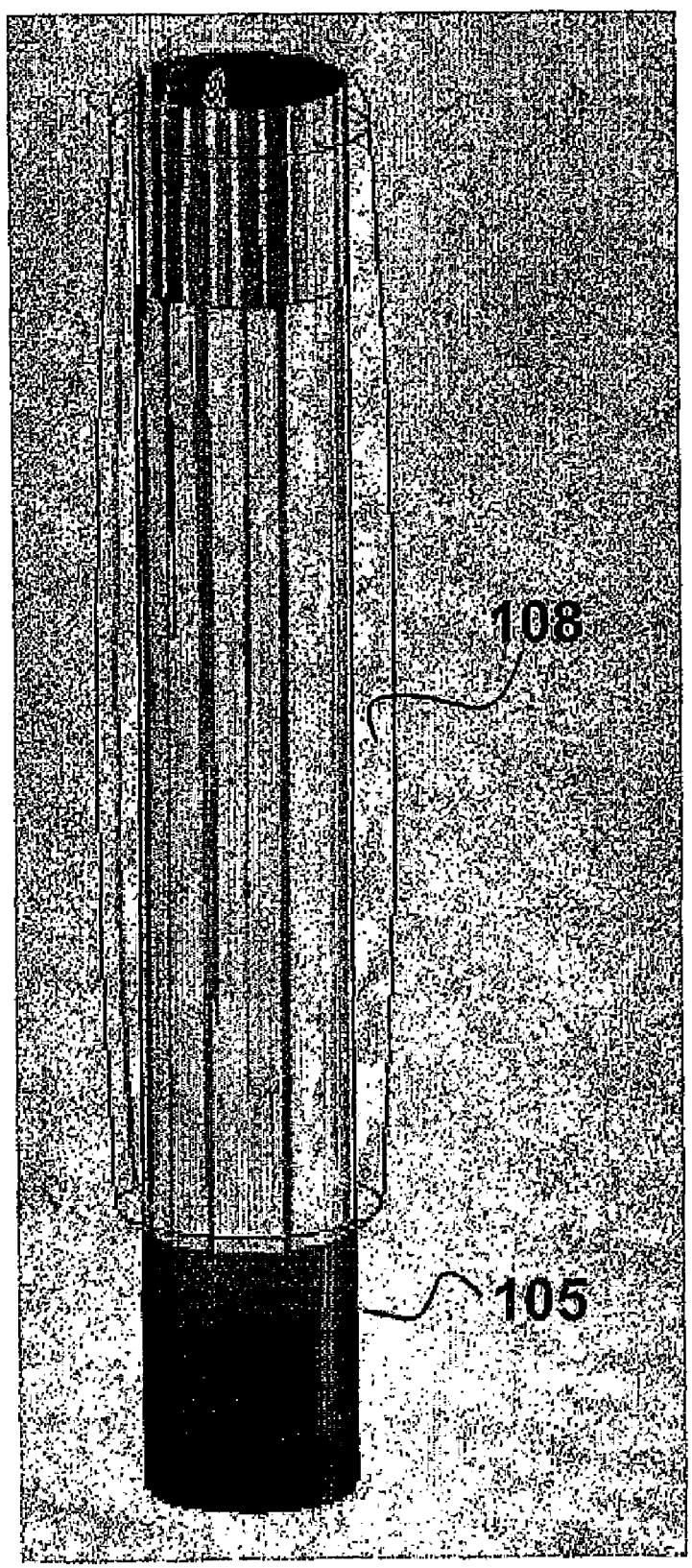
FIG. 13 is an illustration of a distal device in a retracted position, according to an embodiment of the present invention.
Figure 14:
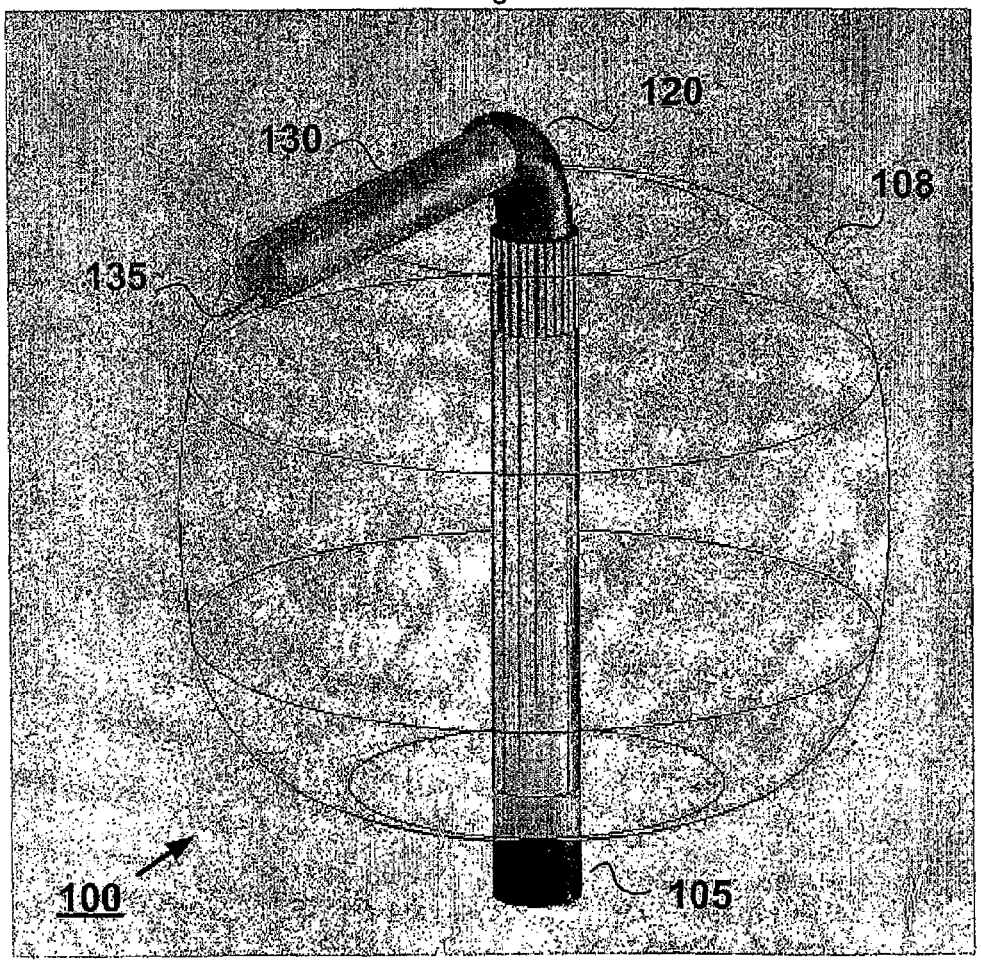
FIG. 14 is an illustration of a distal device in an extended position, according to an embodiment of the present invention.

The outermost sleeve of the distal device 100 is the saline sleeve 105. The saline sleeve 105 runs from the distal end of the device up to a balloon 108 mounted at the top of the distal device 100, as shown in FIG. 13. The saline sleeve 105 is filled with saline to deliver to and inflate the balloon 108, according to a technique known in the art, as shown in FIG. 14. Although the use of saline is described, one having ordinary skill in the art will appreciate that any suitable biocompatible material may be used to inflate the balloon 108.

Upon proper positioning of the distal device 100 relative to the stent-graft, saline is delivered to the balloon 108 by the saline sleeve 105, causing the balloon 108 to inflate, and secure the distal device 100 in place against the stent-graft. According to an embodiment of the present invention, the saline sleeve 105 is made of a soft, flexible material, such as a soft polyurethane material. An exemplary saline sleeve 105 according to an embodiment of the present invention may have an outer diameter of approximately 6 mm and a wall thickness of approximately 0.2 mm.

Concentrically fixed within the saline sleeve 105 is the first sleeve 110. The first sleeve 110 serves as a protective housing for the second sleeve 120, the inner screw sleeve 130, and the inner screw 140, all of which are retracted within the first sleeve 110 during delivery of the distal device 100 into the patient.

One having ordinary skill in the art will appreciate that the first sleeve 110 may be composed of any stiff or rigid material, such as, for example, a stiff polyurethane material. According to an embodiment of the invention, the first sleeve 110 may have an outer diameter of approximately 5.1 mm and a wall thickness of approximately 0.4 mm, which corresponds to an inner diameter of approximately 4.3 mm. The first sleeve 110 includes an upper and a lower portion. The upper portion may be made up of, for example, a stiff rigid polyurethane portion, having an exemplary length of approximately 5 mm. The lower portion of the first sleeve 110 may be made of a soft, bendable polyurethane, to allow the distal device 100 to be maneuvered within the arteries. According to an embodiment of the present invention, the lower portion of the first sleeve 110 connects to and is controlled by a corresponding tube of the connecting system 200. One having ordinary skill in the art will appreciate that the lower portion of the first sleeve 110 may be integrally coupled with a tube of the connecting system 200 or separate, but attachable to the corresponding tube of the connecting system 200.

Slidably inserted within the first sleeve 110 is the second sleeve 120. The second sleeve 120 includes a top and a bottom portion. According to an embodiment of the present invention, the top portion of the second sleeve 120 is extendable out of the first sleeve 110 and out of the tip of the distal device 100. The top portion of the second sleeve 120 may be composed of any stiff yet flexible shape-memory material, such as, for example, a stiff springy nitinol tubing material. According to an embodiment of the present invention, the second sleeve 120 has an outer diameter of approximately 4.3 mm and a wall thickness of approximately 0.4 mm, which corresponds to an inner diameter of approximately 3.5 mm.

The top portion of the second sleeve 120 (i.e., the portion which extends out from the telescoping sleeve arrangement during operation of the distal device 100), has a bent or curved memory shape, as shown in FIG. 18e-18i. As such, extending the second sleeve 120 out from the telescoping sleeve arrangement removes the opposing force of the sleeve housing the second sleeve 120 (i.e., the first sleeve 110), thus allowing the second sleeve 120 to assume its natural bent shaped.

According to an embodiment of the present invention, the top portion of the second sleeve 120 may be bent to a turn radius of approximately 5 mm along its centerline and then shape set in a bent position. FIG. 14 depicts an exemplary second sleeve 120 with the top portion bent, according to an embodiment of the present invention. The second sleeve 120 is capable of being pushed out of the first sleeve 110 to a maximum bend angle of approximately 120 degrees.

According to an embodiment of the present invention, the stiff upper portion of the second sleeve 120 is approximately 15 mm in length. Below the upper portion is a lower portion made up of a soft bendable material, such as polyurethane. Like the lower portion of the first sleeve 110, the lower portion of the second sleeve 120 is connected to and/or integrally formed with a corresponding tube of the connecting system 200. The lower portion of the second sleeve 120 is made of a flexible tubing material and connects the upper portion of the second sleeve 120 to the proximal device 300.

Slidably inserted within the second sleeve 120 is the inner screw sleeve 130. According to an embodiment of the present invention, the inner screw sleeve 130 includes a top and a bottom portion. The top portion of the inner screw sleeve 130, or portion which extends out from the second sleeve 120 upon operation of the distal device 100, is made of a shape-memory material, such as, for example, nitinol. According to a preferred embodiment, the nitinol of the inner screw sleeve 130 is significantly softer and more bendable as compared to the nitinol of the upper portion of the second sleeve 120.

The upper portion of the inner screw sleeve 130 has a substantially straight or non-bent memory shape, as shown in FIG. 14. The inner screw sleeve 130 initially rests in the second sleeve 120 and moves with the second sleeve 120 as the second sleeve 120 is pushed out to its bent position. The inner screw sleeve 130 may include a lip at or near the its top end, which causes the top portion of the inner screw sleeve 130 to extend out of the second sleeve 120 as the second sleeve 120 is pushed against the lip. Once the second sleeve 120 is positioned, the inner screw sleeve 130 is pushed out of the second sleeve 120, thereby allowing the inner screw sleeve 130 to take its substantially straight memory shape.

According to an embodiment of the present invention, the inner screw sleeve 130 may have an outer diameter of approximately 3.5 mm. As discussed in detail above, while the outer profile of the inner screw sleeve 130 is circular, the inner profile of the inner screw sleeve 130 may be an oval, to correspond to the oval shape of the clips 10. According to an embodiment of the present invention, the inner diameter of the inner screw sleeve 130 has a narrow diameter (short diameter of the oval) of approximately 2.1 mm and a wide diameter (long diameter of the oval) of approximately 3.1 mm. According to an embodiment of the present invention, the top portion of the inner screw sleeve 130 has a length of approximately 27 mm.

The lower portion of the inner screw sleeve 130 (i.e., the part of the connecting system 200) is made of a soft bendable material (e.g., polyurethane), similar to the lower portions of the first sleeve 110 and the second sleeve 120.

Extending from a top surface of the inner screw sleeve 130 is a tubular needle 135, as shown in FIGS. 9 and 14. When the inner screw sleeve 130 is pushed up against the stent-graft and target region, the needle 135 penetrates into the two layers and serves as a channel to guide the delivery of the plurality of clips 10. The needle 135 has an inner diameter of sufficiently sized to allow the clip 10 to pass through it. According to an embodiment of the present invention, the needle 135 has an inner diameter of approximately 0.28 mm and an outer diameter of approximately 0.58 mm. According to an embodiment of the invention, the needle 135 has a length greater than the thickness of an average sized aorta wall, such as, for example, a length of approximately 3 mm. Optionally, the needle 135 may include a clip sensor which detects the location of the clips 10 during the deployment process.

Slidably inserted in the inner screw sleeve 130 is the inner screw 140 (described above and depicted in FIG. 7). As shown in FIGS. 7 and 9, the inner screw 140 includes a threaded outer surface having a plurality of threads or teeth. The inner screw 140 has a sufficient number of threads to allow for proper loading of the clips 10 thereon. As such, the number and spacing of the threads on the inner screw 140 depends on the number of clips 10 to be loaded on the inner screw 140. One having ordinary skill in the art will appreciate that the inner screw 140 does not need to have threads along its entire length. According to a preferred embodiment of the present invention, the inner screw 140 has a sufficient number of threads to allow for the loading of twelve clips 10, which corresponds to threads along approximately 65 mm of the inner screw 140.

According to an embodiment of the present invention, the inner screw 140 is rotated by operation of the telescoping sleeves. As the inner screw 140 rotates, the clips 10 are translated upward and out of the tip of the distal device. Each clip 10 exits the distal device 100 via the needle 135, which guides the clip 10 straight out to penetrate into the target region. The clip 10 initially emerges from the tip of the needle 135 in a straightened orientation, penetrates the target, and then forms a secure loop by assuming its curled memory shape once it is free from the constraints of the telescoping sleeves and needle 135 of the distal device 100.

According to an embodiment of the present invention, the inner screw 140 may include a hollow central channel. Using the channel, the distal device 100 may be loaded on a guide wire and maneuvered through the vascular system to the target region. One having ordinary skill in the art will appreciate that the central channel may be any suitable size and shape (e.g., circular).

The inner screw 140 is composed of a soft bendable material, such as polyurethane. According to an embodiment of the present invention, the inner screw 140 has an outer diameter of approximately 1.8 mm (including the thread thickness), or an outer diameter of approximately 1.5 mm (excluding the thread thickness).

On the outside of the first sleeve 110, at the top of the distal device 100, is the balloon 108. One having ordinary skill in the art will appreciate that any suitable biomedical inflatable structure may be used in the present invention, including but not limited to an endovascular balloon manufactured by Cordis Corporation (a Johnson & Johnson company) or Medtronic, Inc. The balloon 108 is filled with saline delivered via the saline sleeve 105 that surrounds the first sleeve 110. According to a preferred embodiment, the balloon 108 may be inflated up to a diameter of approximately 32 mm and have a length of approximately 6 cm down the outside of the first sleeve 110, so that it may expand and press against a large portion of the stent-graft and secure the distal device 100 in place. According to an embodiment of the present invention, the wall of the balloon 108 may have a thickness when inflated of up to 0.45 mm.

FIGS. 13 and 14 depict an exemplary distal device 100 according to an embodiment of the present invention, when in its retracted/deflated and fully extended/inflated positions, respectively. When the distal device 100 is in its retracted position (prior to insertion in the patient), the second sleeve 120, the inner screw sleeve 130, and the inner screw 140 are all recessed into the first sleeve 110, so as to conceal the needle 135 while the distal device 100 is being maneuvered through the patient's vascular system for placement. A schematic of an exemplary distal device 100 according to an embodiment of the invention is depicted in FIG. 9.

As described above, the connecting system 200 of the clip-delivery device 1 connects the sleeves of the distal device 100 to the controls of the proximal device 300. Specifically, the connecting system 200 includes a plurality of tubes that are integrally connected, attached to, or extend from the lower portion of the sleeves of the distal device 100, as described above. Optionally, the plurality of tubes of the connecting system 200 may be housed in a single outer tube, as shown in FIG. 19. According to another option, the connecting system 200 may include suitable means for communicatively connecting the clip sensor of the distal device 100 and the indicator of the proximal device 300, such as, for example, via electrical wire(s). The connecting tubes extend down the length of the vascular system and out of the patient, typically out of the patient's thigh (femoral artery), as shown in FIG. 19. Any movement of a connecting tube at the end outside the patient results in an identical movement of the corresponding sleeve connected at the head of the distal device 100. For example, if one wants to extend the inner screw tube 130 out of the second tube 120 a distance of 1 mm, the connecting tube coupled with the lower portion of inner screw sleeve 130, is pushed up (i.e., toward the distal device 100) a distance of 1 mm. One having ordinary skill in the art will appreciate that the translational and rotational movements of the distal device 100 sleeves may be controlled in a similar manner.

Once the distal device 100 is in place, the proximal device 300 allows the user to control the movement and operation of the sleeves of the distal device 100. Advantageously, the proximal device 300 provides the user with a great deal of control over the operation and movement of the distal device 100, thereby allowing for the selective administration and deployment of the individual clips 10 at a desired location of the target region. The correlated movement between the proximal device 300 and the distal device 100 allows the user to administer one clip 10 at a time, with each clip positioned in a desired relationship relative to previously deployed clips, the stent-graft and the target region.

According to an embodiment of the present invention, the proximal device 300 is a hand held cylinder-like structure having an approximate length of 18 cm. The proximal device 300 has a concave middle, with the ends slightly wider than the center, to make the proximal device 300 easier to grip. In a preferred embodiment, the proximal device 300 is approximately 4.5 cm in diameter in the middle, increasing to approximately 5.5 cm at both ends.

Figure 15:
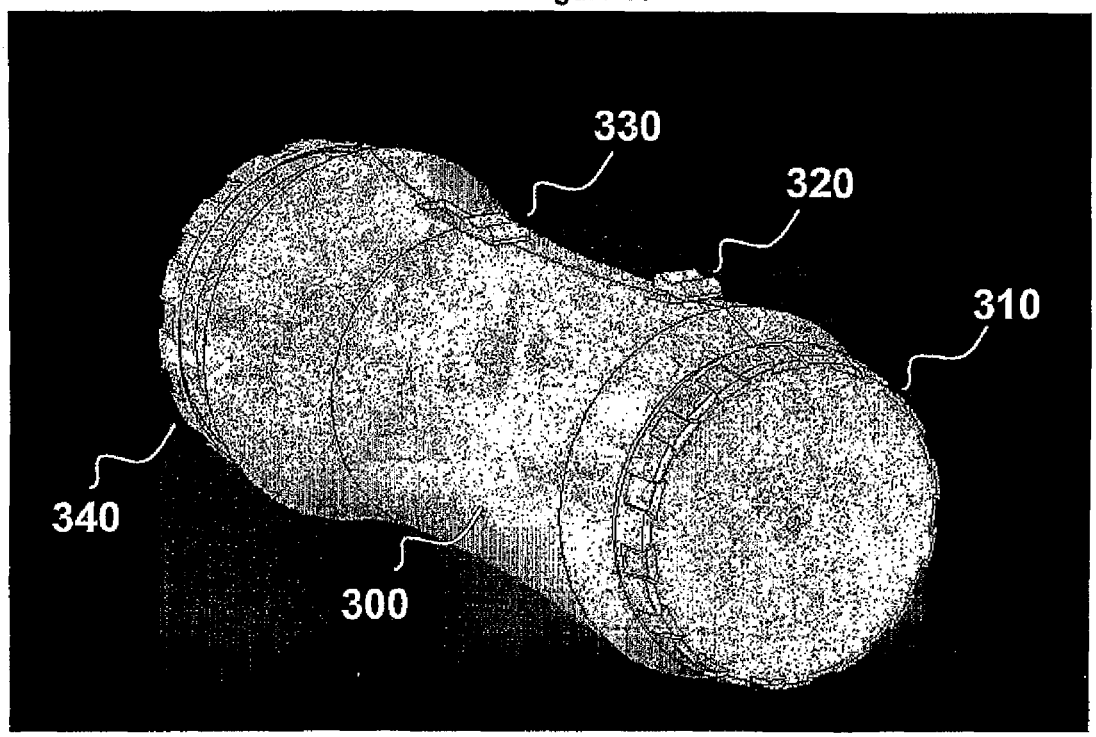
FIG. 15 is an illustration of a proximal device, according to an embodiment of the present invention.
Figure 16:
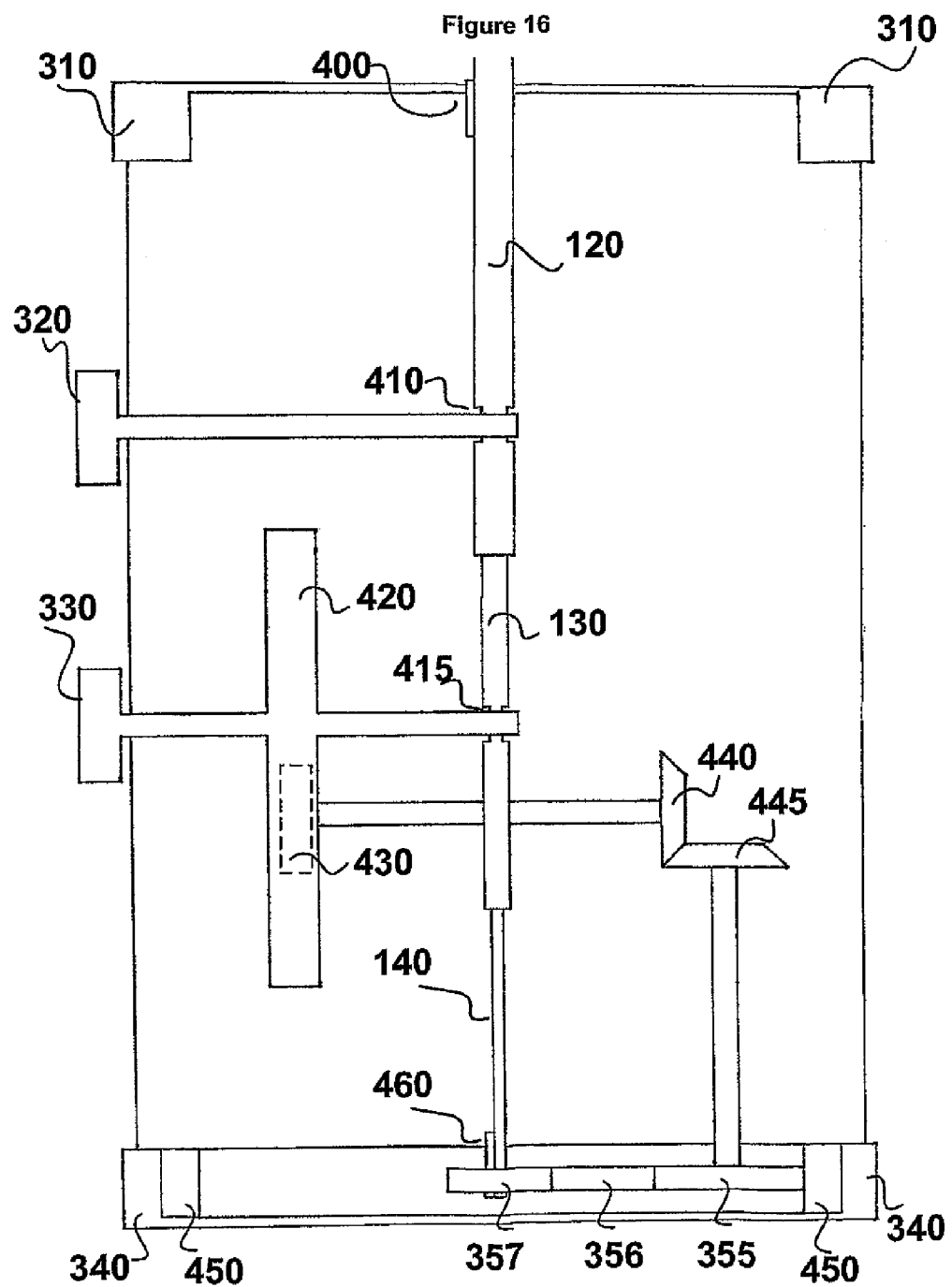
FIG. 16 is a side view of an exemplary control assembly of a proximal device, according to an embodiment of the present invention.

According to an embodiment of the present invention, the proximal device 300 includes a control assembly including two rotating dials, referred to as first dial 310 and second dial 340, and two sliding mechanism or sliders, referred to as first slider 320 and second slider 330. Optionally, the proximal device 300 may include an indicator (e.g., a light) connected to a clip sensor in the needle 135 of the distal device 100. An exemplary proximal device 300 according to an embodiment of the present invention is shown in FIG. 15. FIGS. 16 and 17 illustrate the proximal device 300 as connected to the connecting system 200 and the distal device 100.

In operation, the first dial 310 and the first slider 320 operate the movement of the second sleeve 120. The second slider 330 operates the movement of the inner screw sleeve 130, and the second dial 340 operates the rotation of the inner screw 140.

The first dial 310 is connected to the second sleeve 120 at the head of the proximal device 300, such that, when the first dial 310 is turned, the second sleeve 120 is rotated. The first dial 310 has the freedom to rotate clockwise and counter-clockwise 360 degrees, giving the second sleeve 120 the same freedom. The second sleeve 120 is connected to the first dial 310 via a keyway 400, such that the second sleeve 120 may both slide up and down while rotating under the control of the first dial 310.

According to an embodiment of the present invention, the first slider 320 controls the linear movement of the second sleeve 120. The first slider 320 is set on a track that moves forward and backward and is connected to the second sleeve 120 by a ring that fits around an indented segment 410 of the second sleeve 120. As the first slider 320 moves forward and backward, the second sleeve 120 moves with it (i.e., the second sleeve 120 experiences a corresponding forward or backward movement within the first sleeve 110).

As the second sleeve 120 is pushed out, it causes the inner screw sleeve 130 to move out with it, due to the pushing force exerted on the lip at the top of the inner screw sleeve 130. As such, initially, the inner screw sleeve 130 does not need to be pushed out explicitly, because it is coupled to the forward movement of the second sleeve 120. According to an embodiment of the present invention, on the first slider 320 itself or along an outer surface of the proximal device 300 are a set of incremental markings allowing the user to control and track the amount of movement of the second sleeve 120.

The second slider 330 is set on a track and connected to the inner screw sleeve 130 by a ring around an indented segment 415 of the inner screw sleeve 130 that allows the inner screw sleeve 130 to move linearly up and down. As the second slider 330 moves forward and backward, the inner screw sleeve 130 exhibits a corresponding forward and backward movement within the second sleeve 120. According to an embodiment of the present invention, on the second slider 330 itself or along an outer surface of the proximal device 300 are a set of incremental markings allowing the user to control and track the amount of movement of the inner screw sleeve 130.

Since the inner screw sleeve 130 is initially pushed out by the movement of the second sleeve 120, as the first slider 320 is set to a certain position, the second slider 330 moves along with the first slider 320 to the same position. From here, the second slider 330 may be pushed out further. The second slider 330 includes a rack 420 mounted on its side (within the proximal device 300). When the second slider 330 is shifted to the side, the rack 420 engages on a gear 430. The gear 430 is connected along its axis to a first gear of a 2:1 bevel gear set, referred to as a first bevel gear 440. The bevel gear set transfers the rotation by 90 degrees from the vertical axis of the gear 430 to a new horizontal axis that runs parallel with the length of the proximal device 300. A second bevel gear 445 of the bevel gear set is connected to a shaft through its central axis. The shaft extends to the back of the proximal device 300 and is connected to the first spur gear 455 in the gear train which is part of the mechanism of the second dial 340 that controls the rotation of the inner screw 140. The motion of the second slider 330 and the rotation of the inner screw 140 are coupled together because, following deployment of half of the clip 10, the tip needs to back away from the aorta wall while rotating the rest of the clip 10 out. This is accomplished in a manner that allows the clip 10 to be fully released such that a portion of the clip 10 is embedded inside the stent-graft/aorta wall and the remaining portion is outside the aorta wall. As the second slider 330 is pulled back (coupled with the screw rotation), it pulls the second sleeve 120 back with it, due to lip at the top of the inner screw sleeve 130. Accordingly, as the second slider 330 is pulled back, the first slider 320 moves back with it.

According to an embodiment of the present invention, the second dial 340 is a rotatable dial linked to the inner screw 140. The second dial 340 may be rotated to cause the inner screw 140 to turn and push the clips 10 vertically up the oval shaft of the inner screw sleeve 130. According to an embodiment of the present invention, the second dial 340 includes an internal gear 450 that may be rotated by the operator. The internal gear 450 is part of a gear train along with three spur gears, referred to as first spur gear 455, a second spur gear 456 and a third spur gear 457. The third spur gear 457 is connected to the inner screw 140 at its central axis. According to an embodiment of the present invention, the gear train is in a 1 to 6 ratio, such that when the second dial 340 is rotated halfway, three turns of the clip 10 are pushed out. As the first slider 320 and the second slider 330 move up and out, the inner screw 140 moves with them, due to its connection to the inner screw sleeve 130 at the tip of the distal device 100. In order to allow the inner screw 140 to slide in and out with the inner screw sleeve 130 while being controllable by the second dial 340, the inner screw 140 rests in a keyway 460. The keyway 460 is part of the third spur gear 457, which is rotatable by the second dial 340.

As described above, the purpose of the bevel gear set 440, 445 is to link the backwards motion of the second slider 330 to the rotation of the inner screw 140. One having ordinary skill in the art will appreciate that the gear ratios of the bevel gear set may be selected such that moving the rack back a distance "L" causes the third spur gear 457, with the inner screw 140 in its center, to rotate the inner screw 140 a corresponding distance "L." Thus, the inner screw 140 will end up releasing a length of a clip 10 equal to the distance that the connecting tubes controlling the inner screw tube 130 has been pulled back by the second slider 330. One having ordinary skill in the art will appreciate that the gears used in the present invention may be made of any suitable material, such as, for example, nylon or steel.

At the head of the proximal device 300 is a port into which a suitable saline balloon inflation device, known in the art, may be inserted. The port leads to the saline sleeve 105 that run around the first sleeve 110 up to the balloon 108. According to an embodiment of the present invention, the balloon inflation device may inflate the balloon 108 to a pressure range of approximately four to six atm.

Exemplary arrangements of the elements and connections of the proximal device 300 are shown in FIGS. 16 and 17. One having ordinary skill in the art will appreciate that alternative arrangements, elements and mechanisms may be used in the proximal device 300 without departing from the function and operation of the proximal device 300.

EXAMPLE

The following is a description of an exemplary method of using the clip-delivery device 1, according to an embodiment of the present invention. The steps of the exemplary method are illustrated in FIG. 21.

One having ordinary skill in the art will appreciate that the entire procedure may be monitored using existing x-ray technology. Advantageously, elements of the clip-delivery device 1, such as the clips 10, may be composed of radio-opaque material, thus allowing the position of the distal device 100 to be viewed using conventional x-ray equipment. As such, the surgeon may monitor the emergence and delivery of the each clip 10 and indicates to the surgeon that the process for placing the next clip 10 may be initiated and executed.

Figure 18A:
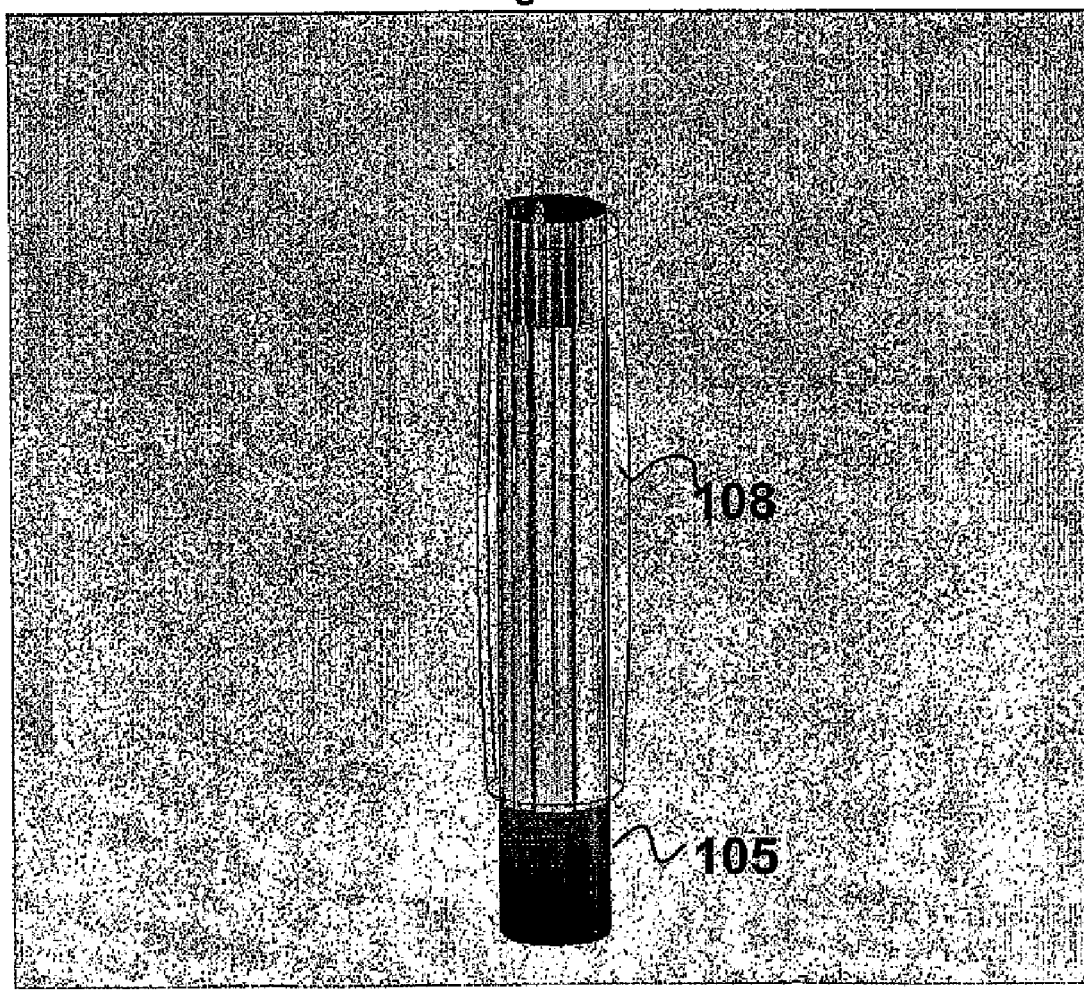
FIGS. 18a-18j are illustrations of a distal device in operation, according to an embodiment of the present invention.

To begin operation of the clip-delivery device 1, the distal device 100 is slipped onto a guide wire that has been placed by a surgeon in a patient. FIGS. 21 and 22 depict the clip-delivery device 1 as inserted in the patient. The distal device 100 is hand-fed to the target region (e.g., an aneurysm and previously positioned stent-graft), in a manner similar to the placement of the implant (e.g., stent-graft). FIG. 18a illustrates an exemplary distal device 100 in its original position.

Figure 18B:
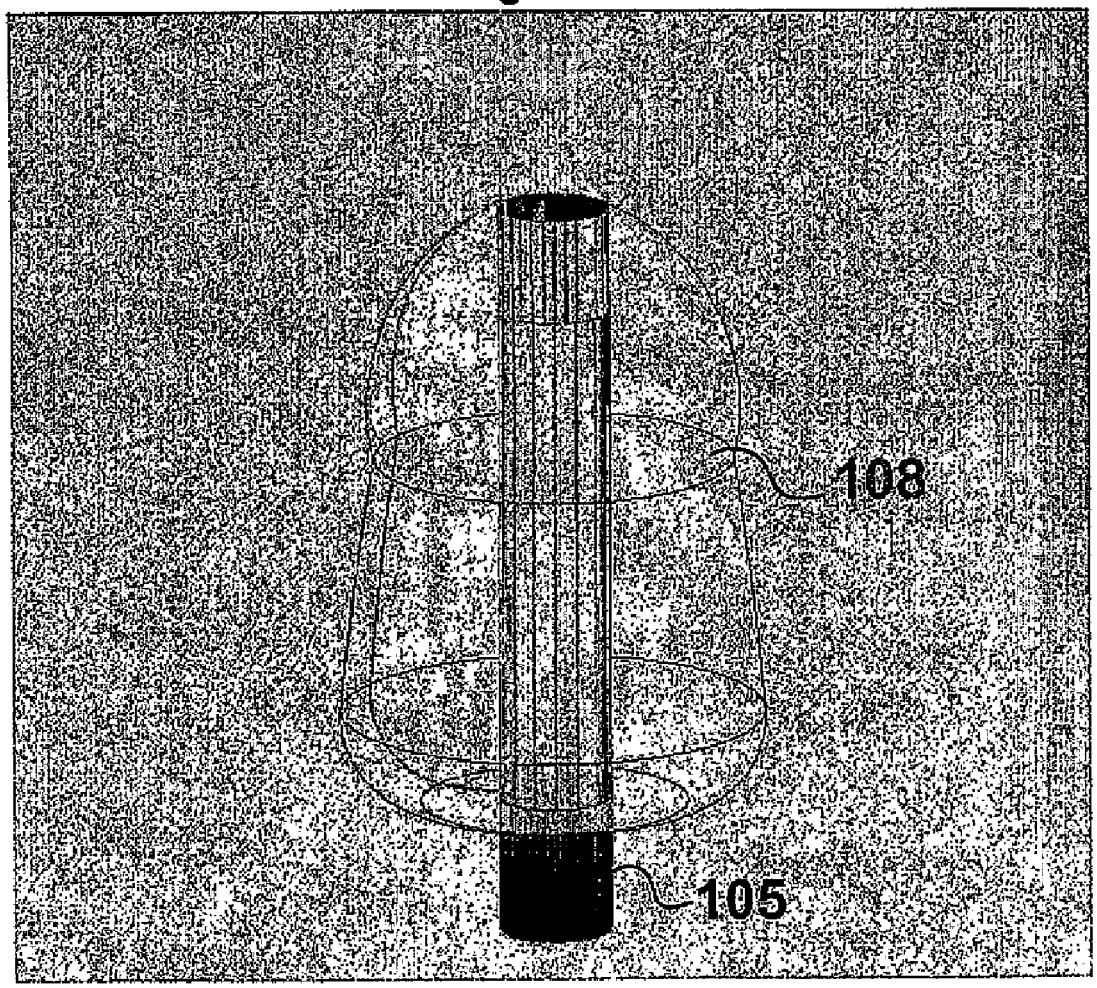
Figure 18C:
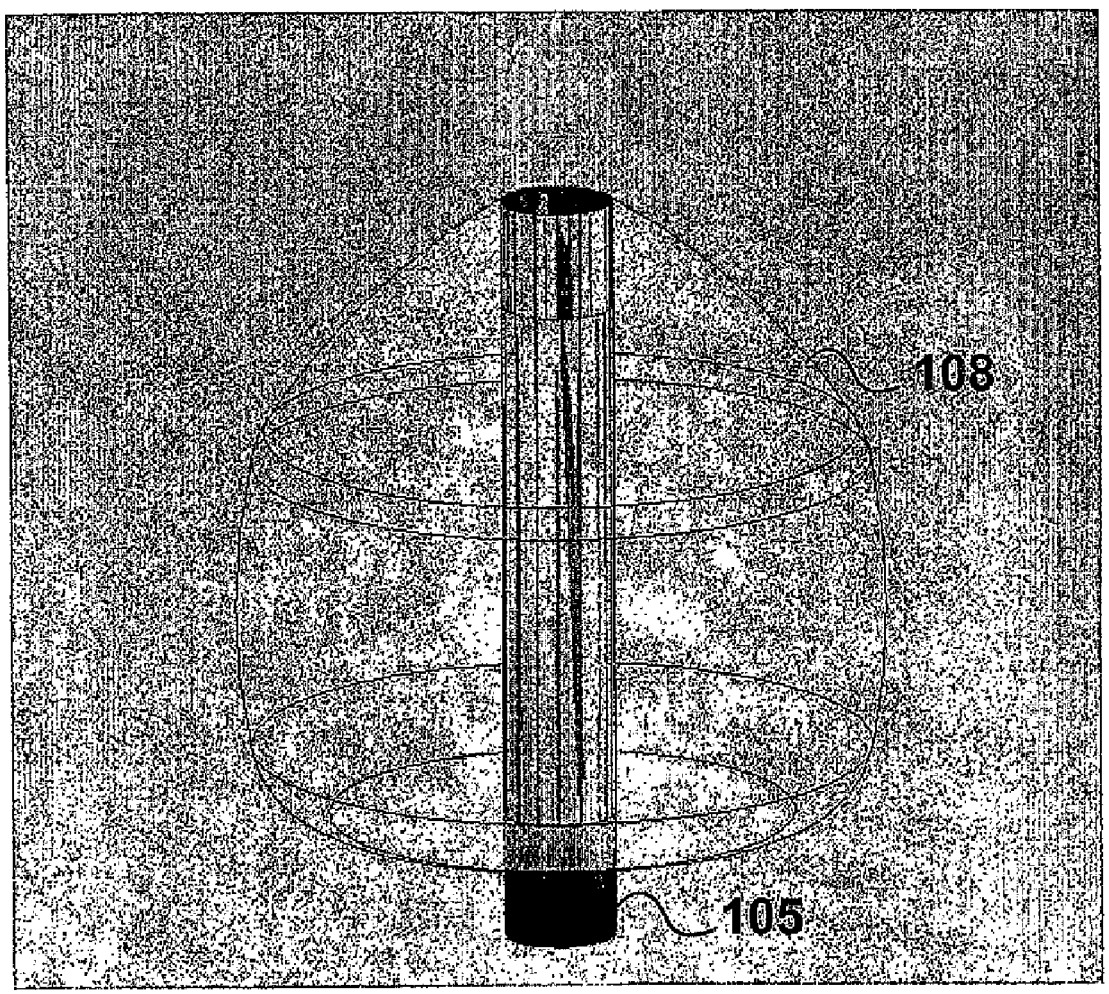
Figure 18D:
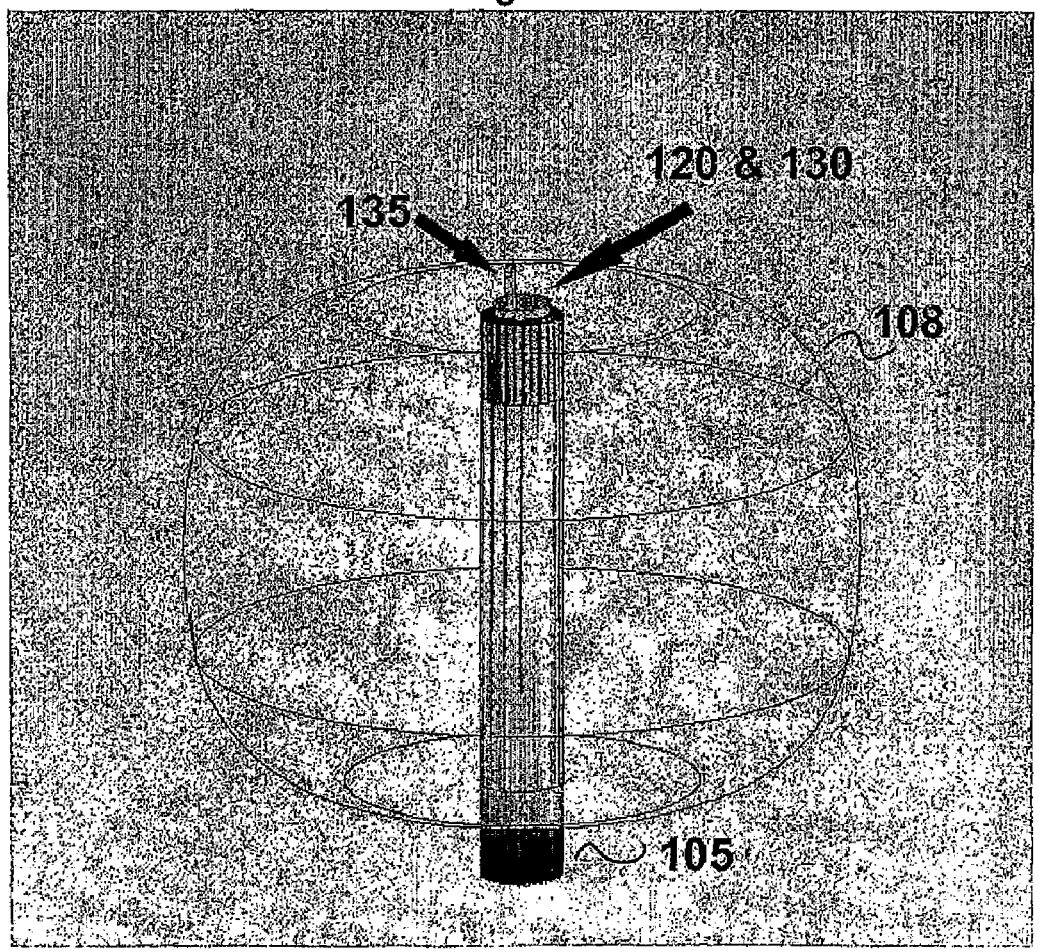
Figure 18E:
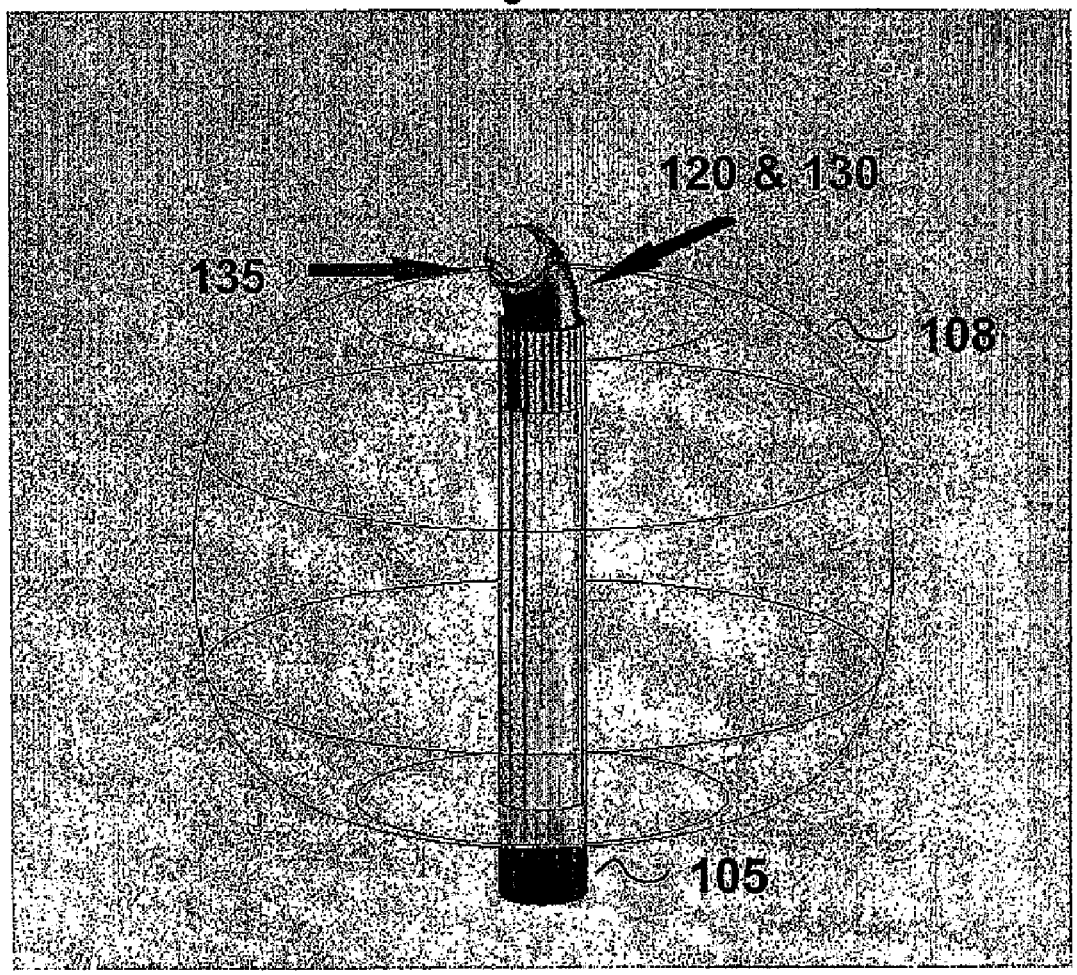

Once the distal device 100 is in an appropriate position at the top end of the stent-graft, the balloon 108 is inflated, causing the distal device 100 to be securely braced against the walls surrounding the target region, as shown in FIGS. 18b and 18c. Next, the surgeon pushes out the second sleeve 120 using the first slider 320. The inner screw sleeve 130 and the second slider 330 also move out as the first slider 320 is pushed out, due to the lip on the inner screw sleeve 130, as shown in FIG. 18d. The second sleeve 120 assumes its memory-set bent shape when it is pushed out of the first sleeve 110, as shown in FIG. 18e. The second sleeve 120 is pushed out to an appropriate angle (i.e., the angle to which the second sleeve 120 is deployed is typically less than 90 degrees for the top ring of the clips 10 and greater than 90 degrees for the bottom ring of the clips 10).

Figure 18F:
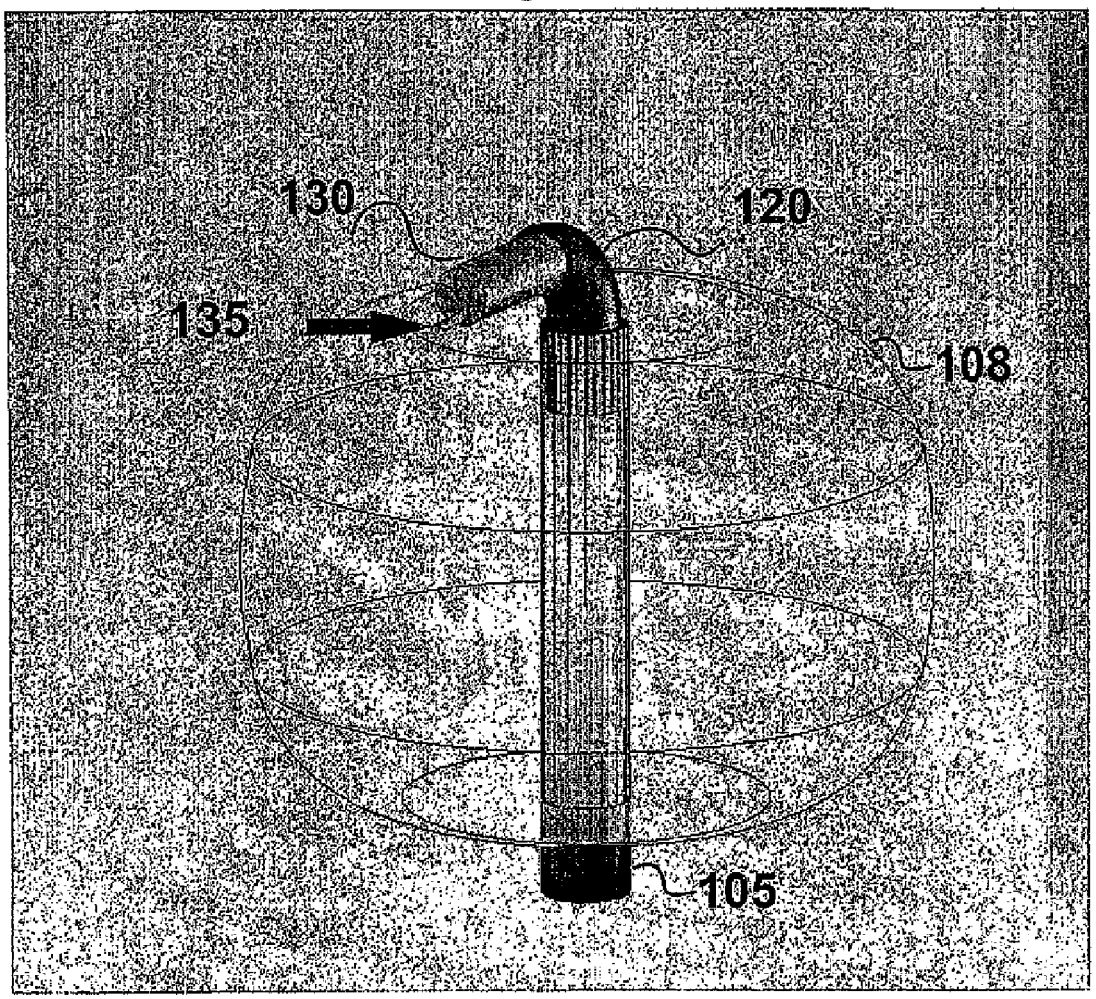
Figure 18G:
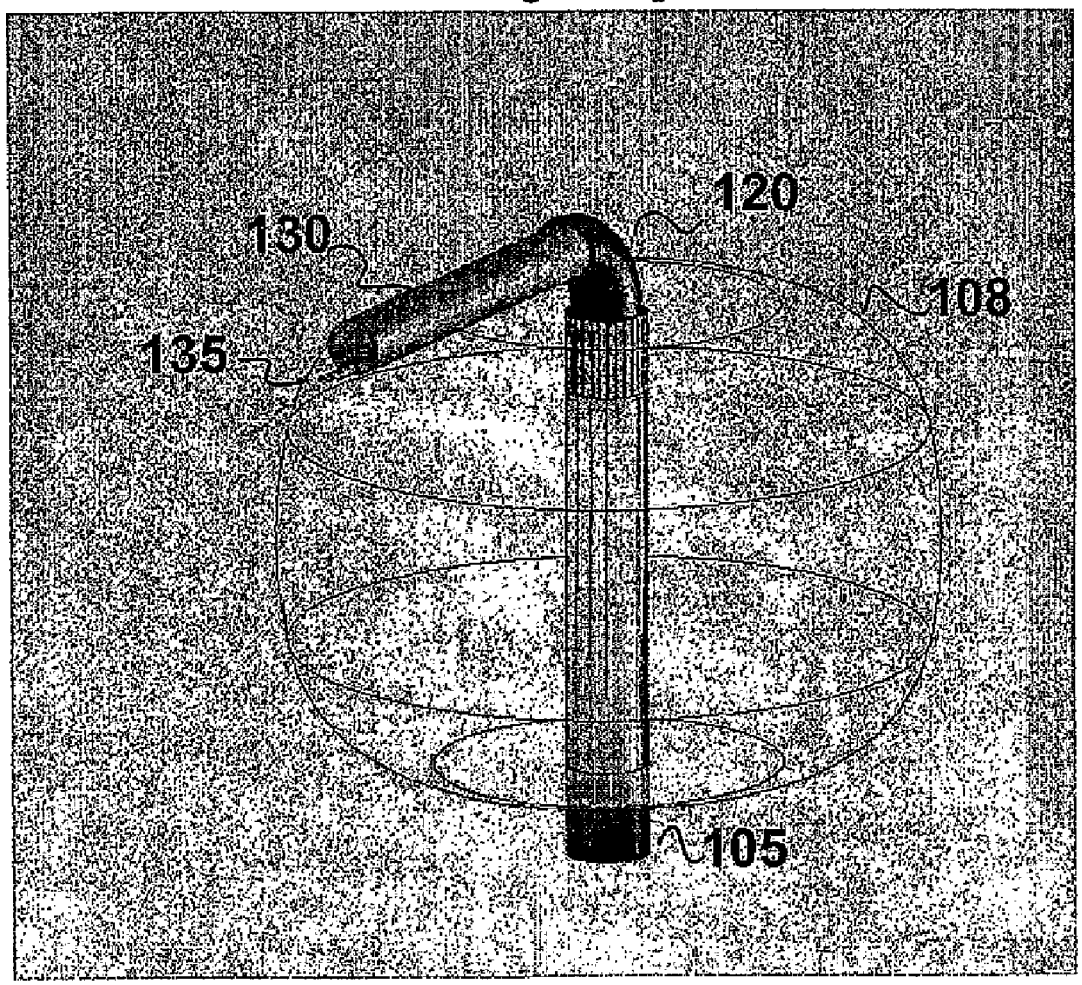

The surgeon then rotates the second sleeve 120 using the first dial 310, until the second sleeve 120 is in a position that is perpendicular to the view of the x-ray imaging device. Next, the second slider 330 is used to push the inner screw sleeve 130 out of the second sleeve 120. When forced out, the inner screw sleeve 130 comes out straightens to its shape-memory property, as shown in FIGS. 18f and 18g. If the second sleeve 120 was successfully rotated to be perpendicular to the x-ray view, then as the inner screw sleeve 130 comes out it will appear to be moving horizontally across the x-ray screen. The surgeon uses the second slider 330 to move the inner screw sleeve 130 out until the needle 135 penetrates the stent-graft and the target region. The surgeon stops pushing up the second slider 330 when he or she sees that the circular top end of the inner screw sleeve 130 is butted up against the stent-graft.

With the device securely in place, and the inner screw sleeve 130 pushed up against the stent-graft, the nitinol spiral clips 10 are deployed by rotating the second dial 340. The second dial 340 causes the inner screw 140 to rotate. When the inner screw 140 turns, the clips 10 move up the inner screw 140 toward the tip of the distal device 100. Each of the spiral clips 10 is funneled through the needle 135, which guides the clip 10 straight out to penetrate into the target region. The clip 10 initially emerges from the tip of the needle 135 in a substantially straight configuration, which facilitates the penetration of the clip into the target stent-graft and/or target region. The clip 10 then forms a secure loop by assuming its curled memory shape once it is free from the constraints of the telescoping sleeves and needle 135. The transformation or curling of the clip 10 into its memory shape causes the clip 10 to firmly embed itself into the implant and/or target region.

The delivery and placement of the plurality of clips 10 may be monitored by the surgeon. According to an exemplary method of monitoring, the radio-opaque nitinol clips 10 are tracked using x-ray technology.

According to an embodiment of the present invention, the location of the clips 10 may be tracked using a clip sensor (e.g., a simple electrical circuit) arranged at or near the exit point of the distal device 100 and a communicatively connected indicator (e.g., a light such as a light emitting diode) arranged on the proximal device 300.

According an embodiment of the present invention, the clip sensor is located at or near the exit point of the needle 135 of the distal device 100. The clip sensor detects when there is a clip 10 present in the needle 135 that is ready to exit the tip. Upon detection of a clip 10 at the exit point of the distal device 100, the clip sensor sends a signal to an indicator (e.g., a light) located on the proximal device 300 to alert the surgeon that a clip 10 is positioned for release from the distal device 100. The indicator remains active while the clip 10 is exiting the needle 135 and turns off only when the clip 10 has been placed at the target region.

According to an embodiment of the present invention, the clip sensor may be any suitable electrical circuit which is 'closed' by the clip 10 when it enters the needle 135. When the circuit is closed, the indicator is activated (i.e., the light is turned on), thus notifying the surgeon that the clip 10 is ready to be deployed. When the clip 10 exits the needle 135 the circuit is returned to an 'open' state, which turns the indicator light off. Although described as an electrical circuit, one having ordinary skill in the art will appreciate that any suitable sensor may be used in conjunction with present invention.

While observing the location of the clip 10, the surgeon rotates the second dial 340 until he or she sees the clip 10 appear outside the tip of the needle 135 and/or the indicator light on the proximal device 300 is activated, at which point the surgeon stops rotating the second dial 340 and takes note of the position of the second dial 340. Then, by rotating the second dial 340 one half turn, three loops of the clip 10 are deployed from the needle 135 to the outside of the aorta wall. With this complete, the surgeon pushes the second slider 330 to the side such that the rack gear 420 engages. The second slider 330 is then pulled back so that as it moves back, it causes all of the connecting gears to rotate. This causes the remainder of the wire of the clip 10 to be pushed out at a rate equal to that of the rate of retraction of the needle 135. This is done so that the needle 135 moving backwards does not accidentally pull the clip 10 back through the target region.

Figure 18H:
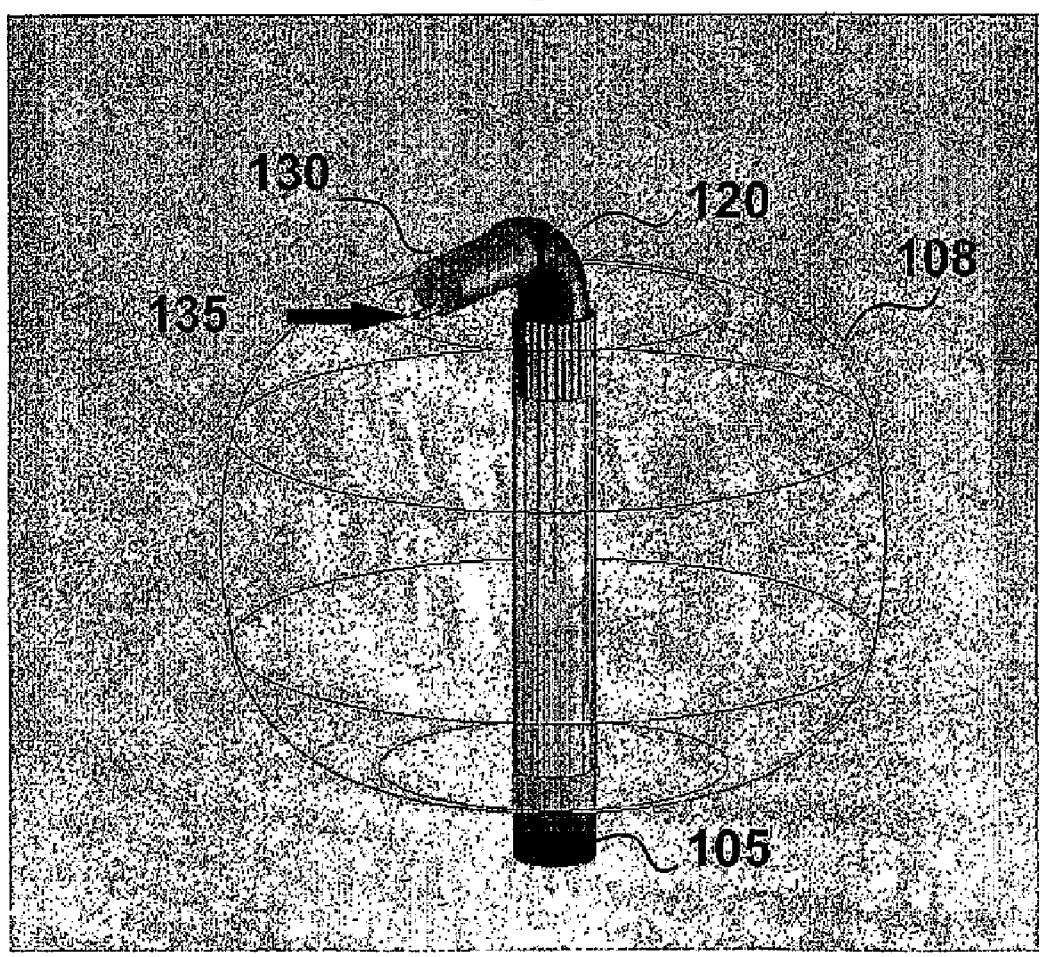
Figure 18I:
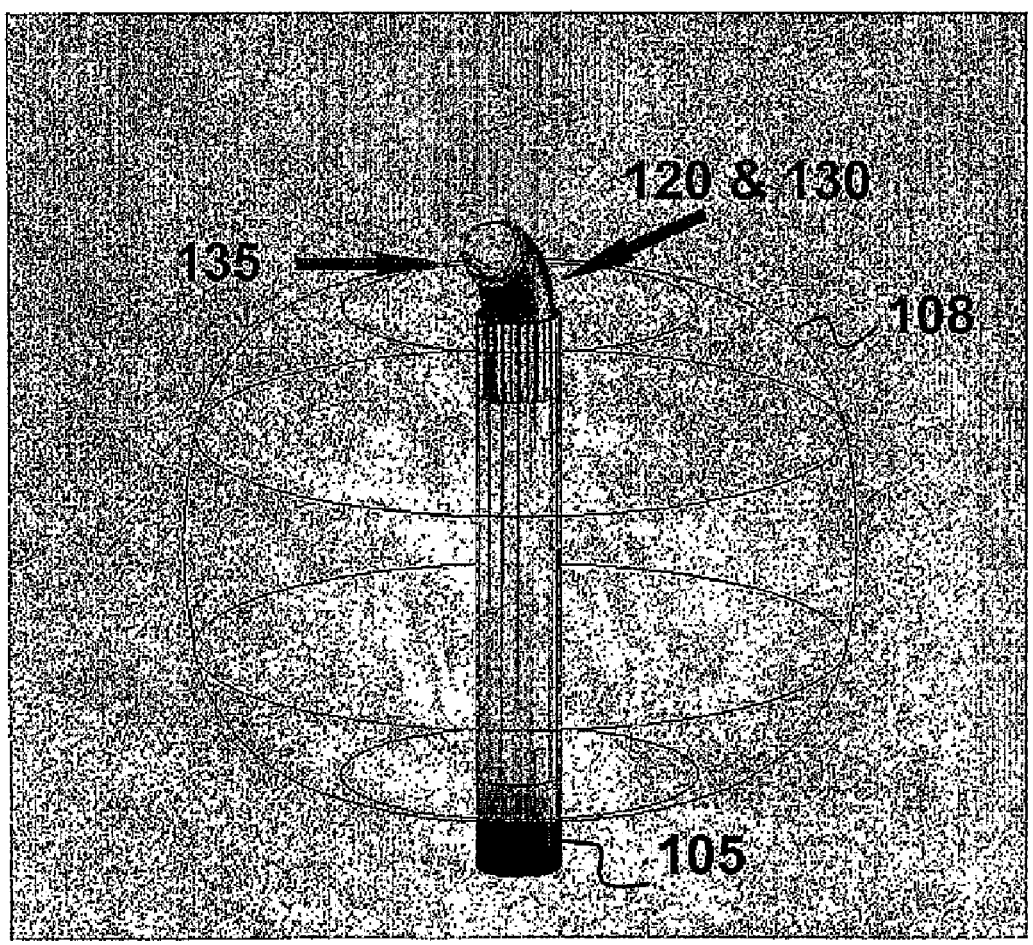
Figure 18J:
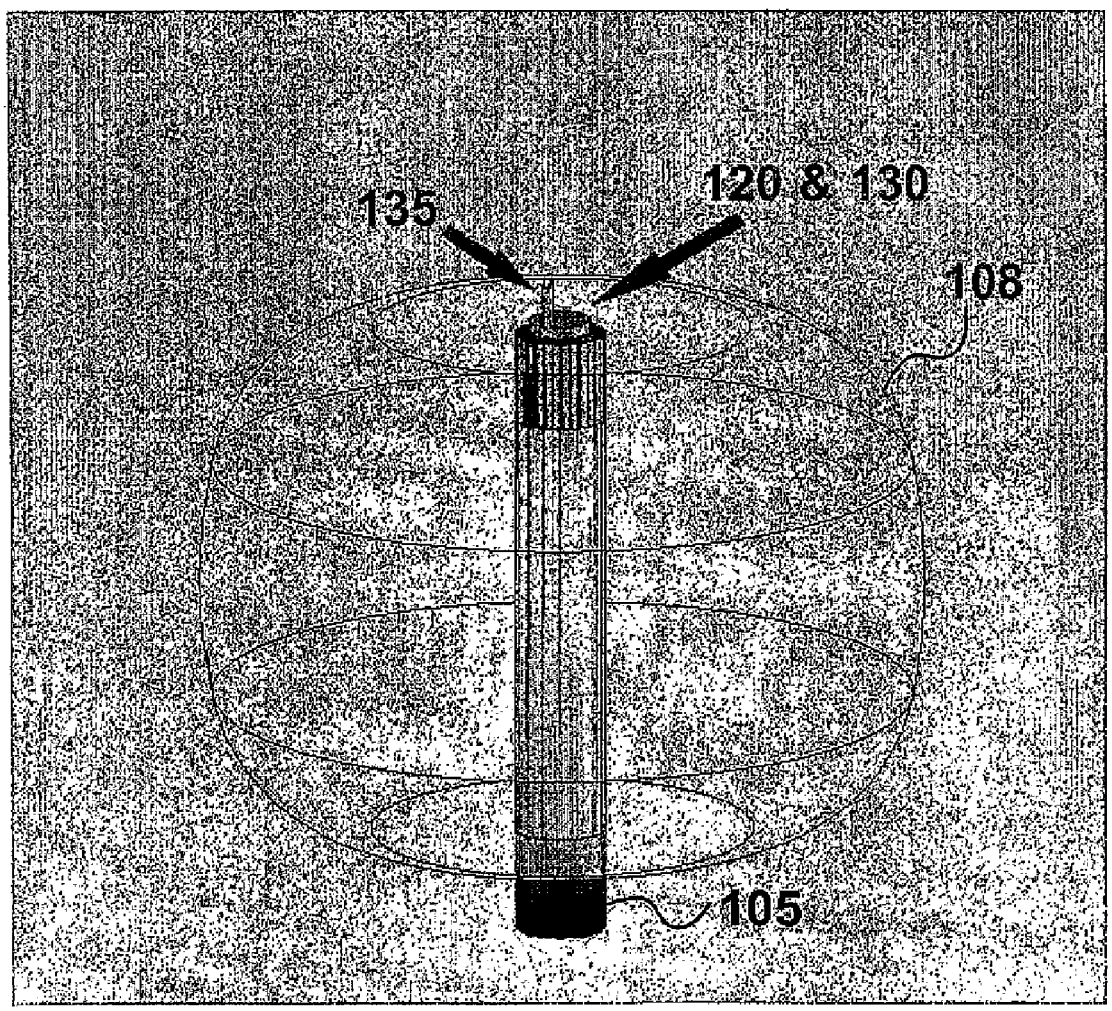

As the second slider 330 is pulled back, it comes to a point where the inner screw sleeve 130 hits the second sleeve 120, as shown in FIGS. 18h and 18i. At this point, if the second slider 330 is pulled back further, it pulls the second sleeve 120 back with it while still causing rotation of the inner screw 140, as shown in FIG. 18j.

At this point, the distal device 100 has released one spiral clip 10 completely. The surgeon now rotates the first dial 310 approximately 60 degrees from its starting point. The surgeon also rotates the x-ray imaging device 60 degrees so that it is now aimed perpendicular to the bend of the second sleeve 120, as it was before. The surgeon then re-positions the second sleeve 120 and the inner screw sleeve 130 for delivery of the next clip 10, and repeats the procedure above for each of the first level of clips 10 (i.e., the level or row of clips 10 placed along the top of the stent-graft).

Once the first level of clips 10 have been placed along the top of the stent-graft, the surgeon repeats the same placement procedure for the lower level of clips 10. To place the lower level of clips 10, the surgeon pushes out the second sleeve 120 to an angle greater than approximately 90 degrees, so that it is lower than the first ring of the spiral clips 10. To initiate placement of the lower level of clips 10, the surgeon rotates the first sleeve 110 by approximately 30 degrees, so that it is at a midpoint of the spiral clips 10 of the top level. The surgeon then proceeds as described above, placing a spiral clip 10 approximately every 60 degrees.

When all the clips 10 have been placed, the inner screw 140, the inner screw sleeve 130, and the second sleeve 120 are fully retracted into the first sleeve 110 and the balloon 108 is deflated. The clip-delivery device 1 may then be removed from the patient.

Although the present invention has been described in considerable detail with reference to certain preferred embodiments and version, other versions and embodiments are possible. Therefore, the scope of the present invention is not limited to the description of the versions and embodiments expressly disclosed herein. The references and disclosure provided in the 'Background of the Invention' section are not admitted to be prior art with respect to the disclosure provided in the present application.

What is claimed is:

1. A clip-delivery device for delivering clips to a target region in a body comprising:
    a distal device comprising a plurality of clips loaded on an inner screw in cooperation with a plurality of telescoping sleeves, wherein operation of the distal device causes the telescoping sleeves to cooperate with one another and the inner screw to deliver each of the plurality of clips out of a needle extending from the inner screw to the target region;
    a proximal device comprising a control assembly configured to control the operation of the distal device; and
    a connecting system comprising a plurality of tubes that interconnect the distal device and the proximal device.

2. The clip-delivery device of claim 1, wherein the plurality of clips are configured to secure an implant to the target region.

3. The clip-delivery device of claim 1, wherein the plurality of clips are formed at least in part with shape-memory material.

4. The clip-delivery device of claim 3, wherein the shape-memory material includes nitinol.

5. The clip-delivery device of claim 4, wherein the nitinol clips have a curled memory shape.

6. The clip-delivery device of claim 3, wherein the shape-memory material clips assume a substantially straight orientation when exiting the needle to facilitate penetration into the target region.

7. The clip-delivery device of claim 3, wherein the shape-memory material clips assume a curled memory shape upon penetration into the target region.

8. The clip-delivery device of claim 1, wherein the telescoping sleeves comprise an inner screw sleeve, a first sleeve, a second sleeve, and a saline sleeve.

9. The clip-delivery device of claim 8, wherein at least a portion of the inner screw sleeve extending from the distal device comprises a shape-memory material having a curled memory shape.

10. The clip-delivery device of claim 9, wherein the shape-memory material is nitinol.

11. The clip-delivery device of claim 8, wherein at least a portion of the second sleeve extending from the distal device comprises a shape-memory material having a bent memory shape.

12. The clip-delivery device of claim 11, wherein the shape-memory material is nitinol.

13. The clip-delivery device of claim 1, wherein the distal device further comprises an inflatable structure at least partially surrounding the plurality of telescoping sleeves.

14. The clip-delivery device of claim 13, wherein the saline sleeve is connected to the inflatable structure and inflates the structure using a biocompatible material delivered from the proximal device.

15. The clip-delivery device of claim 14, wherein the biocompatible material is saline.

16. The clip-delivery device of claim 1, wherein the control assembly comprises a first dial, a second dial, a first slider, and a second slider.

17. The clip-delivery device of claim 16, wherein operation of at least one of the first dial, the second dial, the first slider, and the second slider causes at least one of the plurality of tubes of the connecting system to actuate the telescoping sleeves.

18. The clip-delivery device of claim 1, wherein the inner screw comprises a threaded outer surface adapted to cooperate with the plurality of clips.

19. The clip-delivery device of claim 1, wherein operation of the control assembly causes the plurality of telescoping sleeves to rotate and extend the inner screw outwardly relative to the telescoping sleeves, and wherein the rotation of the inner screw translates each clip linearly up and out of the needle into the target region of the body.

20. The clip-delivery device of claim 1, wherein the distal device comprises a clip sensor for detecting a location of each of the plurality of clips during deployment.

21. The clip-delivery device of claim 20, wherein the proximal device comprises an indicator communicatively connected to the clip sensor for indicating to a user the location of each of the plurality of clips during deployment.

22. The clip-delivery device of claim 1, wherein each of the plurality of clips are delivered to the target region from within a lumen of a vessel.

23. A method for delivering a plurality of clips to a target region in a body, comprising the steps of:
    introducing a distal device into the body including a plurality of clips loaded on an inner screw disposed within a plurality of cooperative telescoping sleeves, wherein the distal device is connected to a proximal device by a connecting system;
    navigating the distal device to a target region of the body;

operating a control assembly of the proximal device to actuate the connecting system and the cooperative telescoping sleeves to extend and rotate the inner screw; and deploying each of the plurality of clips through a needle extended from the inner screw at a desired location of the target region.

24. The method of claim 23, wherein the step of deploying further comprises rotating the plurality of telescoping sleeves to extend and rotate the inner screw, thereby causing each of the plurality of clips to linearly translate along the inner screw and out of the needle.

25. The method of claim 23, further comprising the step of inflating an inflatable structure to secure the distal device in place at the target region.

26. The method of claim 23, wherein the plurality of clips are formed at least in part with a shape-memory material.

27. The method of claim 26, wherein the shape-memory material includes nitinol.

28. The method of claim 23, wherein the plurality of clips are deployed one at a time.

29. The method of claim 23, wherein the plurality of clips secure an implant to the target region.

30. The method of claim 23, further comprising the step of monitoring a location of each of the plurality of clips during the deploying step.

31. The method of claim 23, wherein the step of deploying comprises application of each of the plurality of clips from within a lumen of a vessel.

32. A kit comprising:
a distal device comprising an inner screw adapted to cooperate with a plurality of telescoping sleeves; a plurality of telescoping sleeves adapted to house the inner screw; a plurality of nitinol clips adapted for loading on the inner screw; and a needle extending from the inner screw.

33. The kit of claim 32, wherein the distal device further comprises a clip sensor for detecting a location of the plurality of nitinol clips during deployment.

* * * * *

UNITED STATES PATENT AND TRADEMARK OFFICE
CERTIFICATE OF CORRECTION

| | | |
|---|---|---|
| PATENT NO. | : 8,021,374 B2 | Page 1 of 1 |
| APPLICATION NO. | : 11/814765 | |
| DATED | : September 20, 2011 | |
| INVENTOR(S) | : Bica-Winterling et al. | |

It is certified that error appears in the above-identified patent and that said Letters Patent is hereby corrected as shown below:

Title page Item (22)

The PCT filed date is March 8, 2006. Please replace March 8, 2005 with March 8, 2006.

Signed and Sealed this
Third Day of April, 2012

David J. Kappos
*Director of the United States Patent and Trademark Office*